US007563437B2

(12) United States Patent
Carlsson et al.

(10) Patent No.: US 7,563,437 B2
(45) Date of Patent: Jul. 21, 2009

(54) METHODS AND COMPOSITIONS FOR IMPAIRING MULTIPLICATION OF HIV-1

(75) Inventors: Roland Carlsson, Lund (SE); Elisabeth Sonesson, Lund (SE); Yvonne Stenberg, Akarp (SE); Leif Strandberg, Kavlinge (SE); Gideon Goldstein, Short Hills, NJ (US)

(73) Assignee: Thymon, LLC, Short Hills, NJ (US)

( * ) Notice: Subject to any disclaimer, the term of this patent is extended or adjusted under 35 U.S.C. 154(b) by 66 days.

(21) Appl. No.: 11/353,293

(22) Filed: Feb. 13, 2006

(65) Prior Publication Data

US 2006/0211108 A1    Sep. 21, 2006

Related U.S. Application Data

(60) Provisional application No. 60/653,263, filed on Feb. 15, 2005.

(51) Int. Cl.
A61K 39/395        (2006.01)
(52) U.S. Cl. .................................... 424/130.1
(58) Field of Classification Search .................. None
See application file for complete search history.

(56) References Cited

U.S. PATENT DOCUMENTS

| | | | |
|---|---|---|---|
| 4,405,712 A | 9/1983 | van de Woude et al. |
| 4,735,896 A | 4/1988 | Wang et al. |
| 4,738,922 A | 4/1988 | Haseltine et al. |
| 4,833,072 A | 5/1989 | Krchnak et al. |
| 4,839,288 A | 6/1989 | Montagnier et al. |
| 4,871,488 A | 10/1989 | Mannino |
| 4,888,290 A | 12/1989 | Kortright et al. |
| 4,981,790 A | 1/1991 | Haseltine et al. |
| 4,983,387 A | 1/1991 | Goldstein et al. |
| 5,019,510 A | 5/1991 | Wain-Hobson |
| 5,026,635 A | 6/1991 | Ferguson et al. |
| 5,043,262 A | 8/1991 | Haseltine et al. |
| 5,110,802 A | 5/1992 | Cantin |
| 5,158,877 A | 10/1992 | Edwards |
| 5,166,050 A | 11/1992 | Shriver et al. |
| 5,238,822 A | 8/1993 | Dykes |
| 5,306,614 A | 4/1994 | Alizon et al. |
| 5,476,765 A | 12/1995 | Wang et al. |
| 5,527,894 A | 6/1996 | Gold et al. |
| 5,597,895 A | 1/1997 | Gaynor |
| 5,606,026 A | 2/1997 | Rodman |
| 5,652,122 A | 7/1997 | Frankel et al. |
| 5,654,195 A | 8/1997 | Sodroski et al. |
| 5,670,617 A | 9/1997 | Frankel et al. |
| 5,674,980 A | 10/1997 | Frankel |
| 5,677,143 A | 10/1997 | Gaynor et al. |
| 5,686,264 A | 11/1997 | Gaynor et al. |
| 5,747,641 A | 5/1998 | Frankel et al. |
| 5,773,247 A | 6/1998 | Maeda et al. |
| 5,773,602 A | 6/1998 | Alizon et al. |
| 5,789,531 A | 8/1998 | Sumner-Smith et al. |
| 5,801,056 A | 9/1998 | Haseltine et al. |
| 5,804,604 A | 9/1998 | Frankel et al. |
| 5,821,046 A | 10/1998 | Karn et al. |
| 5,830,634 A | 11/1998 | Brust et al. |
| 5,831,034 A | 11/1998 | Katinger et al. |
| 5,861,243 A | 1/1999 | Dietrich et al. |
| 5,866,694 A | 2/1999 | Katinger et al. |
| 5,889,175 A | 3/1999 | Mehtali et al. |
| 5,891,994 A | 4/1999 | Goldstein |
| 6,001,977 A | 12/1999 | Chang et al. |
| 6,024,965 A | 2/2000 | van Baalen et al. |
| 6,193,981 B1 | 2/2001 | Goldstein |
| 6,399,067 B1 | 6/2002 | Goldstein |
| 6,524,582 B2 | 2/2003 | Goldstein |
| 6,525,179 B1 | 2/2003 | Goldstein |
| 7,008,622 B2 | 3/2006 | Goldstein |
| 2003/0166832 A1 | 9/2003 | Goldstein |
| 2003/0180326 A1 | 9/2003 | Goldstein |
| 2003/0194408 A1 | 10/2003 | Goldstein |
| 2005/0245454 A1 | 11/2005 | Goldstein |

FOREIGN PATENT DOCUMENTS

| | | |
|---|---|---|
| EP | 273716 | 7/1988 |
| EP | 306219 | 3/1989 |
| WO | WO-87/02989 | 5/1987 |
| WO | WO-91/09958 | 7/1991 |
| WO | WO-91/10453 | 7/1991 |
| WO | WO-92/07871 | 5/1992 |

(Continued)

OTHER PUBLICATIONS

Ruckwardt et al., Sequence Variation within the Dominant Amino Terminus Epitope Affects Antibody Binding and Neutralization of Human Immunodeficiency Virus Type 1 Tat Protein, Journal of Virology, Dec. 2004, 78(23):13190-13196.*

(Continued)

*Primary Examiner*—Bruce Campell
*Assistant Examiner*—Nicole Kinsey White
(74) *Attorney, Agent, or Firm*—Howson & Howson LLP

(57) ABSTRACT

A single isolated antibody or antibody fragment thereof binds to multiple variant sequences within an epitope of HIV-1 Tat protein displayed in multiple strains and subtypes of HIV-1. This "pan-epitope" antibody is useful in therapeutic and prophylactic compositions and treatments of HIV-1 infection, regardless of strain. This pan-epitope antibody is useful in assays for the detection of levels of HIV-1 based on a measurement of the amount of Tat protein in a biological sample.

9 Claims, 7 Drawing Sheets

FOREIGN PATENT DOCUMENTS

| WO | WO-92/14755 | 9/1992 |
|---|---|---|
| WO | WO-94/15634 | 7/1994 |
| WO | WO-95/31999 | 11/1995 |
| WO | WO-97/34617 | 9/1997 |
| WO | WO-98/14587 | 4/1998 |
| WO | WO-99/09056 | 2/1999 |
| WO | WO-99/45959 | 9/1999 |
| WO | WO-01/82944 | 11/2001 |
| WO | WO-2004/056316 | 7/2004 |
| WO | WO-2005/062871 | 7/2005 |

OTHER PUBLICATIONS

Goldstein et al., Two B cell epitopes of HIV-1 Tat protein have limited antigenic polymorphism in geographically diverse HIV-1 strains, Vaccine, 2001, 19:1738-1746.*

Aldovini et al, "Synthesis of the Complete Trans-Activation Gene Product of Human T-Lymphotropic Virus Type III in *Escherichia coli*: Demonstration of Immunogenicity in vivo and Expression in vitro", Proc. Natl. Acad. Sci. USA, 83:6672-6676 (Sep. 1986).

Baumberger et al, "High Levels of Circulating RNA in Patients with Symptomatic HIV-1 Infection", AIDS, 7(Suppl. 2):S59-S64 (Nov. 1993).

Brake et al, "Characterization of Murine Monoclonal Antibodies to the tat Protein from Human Immunodeficiency Virus Type 1", J. Virol., 64(2):962-965 (Feb. 1990).

Cafaro et al., "Control of SHIV-89. 6P-Infection of Cynomolgus Monkeys by HIV-1 Tat Protein Vaccine", Nat. Med., 5(6):643-650 (Jun. 1999).

Calarota et al., "Cellular Cytoxic Response Induced by DNA Vaccination in HIV-1 Injected Patients", Lancet, 351:1320-1325 (May 1998).

Caselli et al., "DNA Immunization with HIV-1 tat Mutated in the trans Activation Domain Induces Humoral and Cellular Immune Response Against Wild-Type Tat", J. Immunol., 162:5631-5638 (May 1999).

Clerici et al, "T-Cell Proliferation to Subinfectious SIV Correlates with Lack of Infection after Challenge of Macaques", AIDS, 8(10):1391-1395 (Oct. 1994).

Cohen et al., "Pronounced Acute Immunosuppression in vivo Mediated by HIV tat Challenge", Proc. Natl. Acad. Sci., USA, 96(19):10842-10847 (Sep. 1999).

Coombs et al, "Association of Plasma Human Immunodeficiency Virus Type 1 RNA Level with Risk of Clinical Progression in Patients with Advanced Infection", J. Infect. Dis., 174:704-712 (Oct. 1996).

Daniel et al, "Protective Effects of a Live Attenuated SIV Vaccine with a Deletion in the nef Gene", Science, 258:1938-1941 (Dec. 18, 1992).

Fawell et al, "Tat-Mediated Delivery of Heterologous Proteins into Cells", Proc. Natl. Acad. Sci. USA, 91:664-668 (Jan. 1994).

Frankel et al, "Activity of Synthetic Peptides from the Tat Protein of Human Immunodeficiency Virus Type 1", Proc. Natl. Acad. Sci. USA, 86:7397-7401 (Oct. 1989).

Goldstein, "HIV-1 Tat Protein as a Potential AIDS Vaccine", Nat. Med., 2(9):960-964 (Sep. 1996).

Goldstein et al., "Two B Cell Epitopes of HIV-1 Tat protein have Limited Antigenic Polymorphism in Geographically Diverse HIV-1 Strains", Vaccine, 19(13-14):1738-1746 (Feb. 8, 2001).

Goldstein et al., "Minimization of Chronic Plasma Viremia in Rhesus Macaques Immunized with Synthetic HIV-1Peptides and Infected with a Chimeric Simian/Human Immunodeficiency Virus (SHIV33)", Vaccine, 18:2789 (Jun. 2000).

Gringeri et al., "Safety and Immunogenicity of HIV-1 Tat Toxoid in Immunocompromised HIV-1 Infected Patients", J. Hum. Virol., 1(4):293-298 (May/Jun. 1998).

Harlow et al, "Antibodies, a Laboratory Manual", pp. 96-97 (1988).

Haynes, "Scientific and Social Issues of Human Immunodeficiency Virus Vaccine Development", Science, 260:1279-1286 (May 28, 1993).

Hinkula et al, "Recognition of Prominent Viral Epitopes Induced by Immunization with Human Immunodeficiency Virus Type 1 Regulatory Genes", J. Virol., 71(7):5528-5539 (Jul. 1997).

Krone et al, "Natural Antibodies to HIV-tat Epitopes and Expression of HIV-1 Genes in Vivo", J. Med. Virol., 26:261-270 (Nov. 1988).

Kusumi et al, "Human Immunodeficiency Virus Type 1 Envelope Gene Structure and Diversity in vivo and after Cocultivation in vitro", J. Virol., 66(2):875-885 (Feb. 1992).

Larder et al, "HIV with Reduced Sensitivity to Zidovudine (AZT) Isolated During Prolonged Therapy", Science, 243:1731-1733 (Mar. 31, 1989).

Lee et al, "Circulating HIV-1-Infected Cell Burden from Seroconversion to AIDS: Importance of Postseroconversion Viral Load on Disease Course", J. Acq. Imm. Def. Synd., 7(4):381-388 (Apr. 1994).

Letvin, "Vaccines Against Human Immunodeficiency Virus—Progress and Prospects", N. Engl. J. Med., 329(19):1400-1405 (Nov. 4, 1993).

Li et al, "Tat Protein Induces Self-Perpetuating Permissivity for Productive HIV-1 Infection", Proc. Natl. Acad. Sci. USA, 94:8116-8120 (Jul. 1997).

Mann et al, "Endocytosis and Targeting of Exogenous HIV-1 Tat Protein", EMBO J., 10(7):1733-1739 (Jul. 1991).

McPhee et al, "Recognition of Envelope and tat Protein Synthetic Peptide Analogs by HIV Positive Sera or Plasma", FEBS Letters, 233(2):393-396 (Jun. 1988).

Mellors et al, "Prognosis in HIV-1 Infection Predicted by the Quantity of Virus in Plasma", Science, 272:1167-1170 (May 24, 1996).

Meyerhans et al, "Temporal Fluctuations in HIV Quasispecies in vivo are not Reflected by Sequential HIV Isolations", Cell, 58:901-910 (Sep. 8, 1989).

Osborn, "The Rocky Road to an AIDS Vaccine", J. Acq. Imm. Def. Syndr. Hum. Retrovirol., 9(1):26-29 (May 1995).

Paul, "Can the Immune Response Control HIV Infection?", Cell, 82:177-182 (Jul. 28, 1995).

Pilkington et al, "Recombinant Human Fab Antibody Fragments to HIV-1 REV and TAT Regulatory Proteins: Direct Selection from a Combinatorial Phage Display Library", Mol. Immunol., 33(4/5):439-450 (Mar.-Apr. 1996).

Preston et al, "Fidelity of HIV-1 Reverse Transcriptase", Science, 242:1168-1171 (Nov. 25, 1988).

Ramakrishna et al., "Codon Optimization of the Tat Antigen of Human Immunodeficiency Virus Type 1 Generates Strong Immune Responses in Mice following Genetic Immunization", J. Virol., 78(17):9174-9189 (Sep. 2004).

Re et al, "Effect of Antibody to HIV-1 Tat Protein on Viral Replication in Vitro and Progression of HIV-1 Disease in Vivo", J. Acq. Imm. Def. Synd. Hum. Retrovirol., 10(4):408-416 (Dec. 1, 1995).

Roberts et al, "The Accuracy of Reverse Transcriptase from HIV-1", Science, 242:1171-1173 (Nov. 25, 1988).

Ruckwardt et al., "Sequence Variation within the Dominant Amino Terminus Epitope Affects Antibody Binding and Neutralization of Human Immunodeficiency Virus Type 1 Tat Protein" J. Virol., 78(23):13190-13196 (Dec. 2004).

Saag et al, "Hiv Viral Load Markers in Clinical Practice", Nat. Med., 2(6):625-629 (Jun. 1996).

Saag et al, "A Short-Term Clinical Evaluation of L-697,661, a Non-Nucleoside Inhibitor of HIV-1 Reverse Transcriptase", N. Engl. J. Med., 329(15):1065-1072 (Oct. 7, 1993).

Saksela et al, "Human Immunodeficiency Virus Type 1 mRNA Expression in Peripheral Blood Cells Predicts Disease Progression Independently of the Numbers of CD4+ Lymphocytes", Proc. Natl. Acad. Sci. USA, 91:1104-1108 (Feb. 1994).

Sande et al, "Antiretroviral Therapy for Adult HIV-Infected Patients", JAMA, 270(21):2583-2589 (Dec. 1, 1993).

Seligmann et al, "Concorde: MRC/ANRS Randomised Double-Blind Controlled Trial of Immediate and Deferred Zidovudine in Symptom-free HIV Infection", Lancet, 343:871-881 (Apr. 9, 1994).

Steinaa et al, "Antibody to HIV-1 Tat Protein Inhibits the Replication of Virus in Culture", Arch. Virol., 139:263-271 (1994).

Suzue et al, "Adjuvant-Free hsp70 Fusion Protein System Elicits Humoral and Cellular Immune Responses to HIV-1 p24", J. Immunol., 156:873-879 (Jan. 15, 1996).

Tam, "Synthetic Peptide Vaccine Design: Synthesis and Properties of a High-Density Multiple Antigenic Peptide System", Proc. Natl. Acad. Sci. USA, 85:5409-5413 (Aug. 1988).

Tikhonov et al., "Tat-Neutralizing Antibodies in Vaccinated Macaques", J. Virol., 77(5):3157-3166 (Mar. 2003).

Tindall et al, "Primary HIV Infection: Host Responses and Intervention Strategies", AIDS, 5(1):1-14 (Jan. 1991).

Welles et al, "Prognostic Value of Plasma Human Immunodeficiency Virus Type 1 (HIV-1) RNA Levels in Patients with Advanced HIV-1 Disease and with Little or No Prior Zidovudine Therapy", J. Infect. Dis., 174:696-703 (Oct. 1996).

Wolinsky et al, "Adaptive Evolution of Human Immunodeficiency Virus-Type 1 During the Natural Course of Infection", Science, 272:537-542 (Apr. 26, 1996).

Zauli et al, "An Autocrine Loop of HIV Type-1 Tat Protein Responsible for the Improved Survival/Proliferation Capacity of Permanently Tat-Transfected Cells and Required for Optimal HIV-1 LTR Transactivating Activity", J. Acq. Imm. Def. Synd. Hum. Retrovirol., 10(3):306-316 (Nov. 1, 1995).

Webster's Ninth New Collegiate Dictionary, p. 602 (1990).

\* cited by examiner

METHODS AND COMPOSITIONS FOR IMPAIRING MULTIPLICATION OF HIV-1

CROSS-REFERENCE TO RELATED APPLICATIONS

This application claims the benefit of the priority of U.S. Provisional Patent Application No. 60/653,263, filed Feb. 15, 2005.

BACKGROUND OF THE INVENTION

The present invention relates generally to compositions and methods useful for inhibiting the multiplication of human immunodeficiency virus-1 (HIV-1) in chronically infected patients, symptomatic or asymptomatic, thus minimizing progression to AIDS.

A variety of therapeutic methods are currently employed or under investigation to treat patients infected with human immunodeficiency virus (HIV-1). Certain approaches to HIV-1 treatment have focused on the transactivating (tat) gene of HIV-1, which produces a protein (Tat) essential for high levels of transcription of the virus. The tat gene and its protein have been sequenced and examined for involvement in proposed treatments of HIV (see, e.g., the documents cited in U.S. Pat. No. 6,525,179). Tat protein is released extracellularly, making it available to be taken up by other infected cells to enhance transcription of HIV-1 in the cells and to be taken up by noninfected cells, altering host cell gene activations and rendering the cells susceptible to infection by the virus. Uptake of Tat by cells is very strong, and has been reported as mediated by a short basic sequence of the protein (S. Fawell et al., 1994 Proc. Natl. Acad. Sci., USA, 91:664-668).

Both monoclonal and polyclonal antibodies to Tat protein have been readily produced in animals and shown to block uptake of Tat protein in vitro and such monoclonal or polyclonal antibodies to Tat protein added to tissue culture medium have attenuated HIV-1 infection in vitro (see, e.g., documents cited in U.S. Pat. No. 6,524,582).

Prior scientific publications and patent publications by one of the present co-inventors (e.g., G. Goldstein, 1996 Nature Med., 2:960; G. Goldstein, 2000 Vaccine, 18:2789; International Patent Publication No. WO 95/31999, published Nov. 30, 1995; International Patent Publication No. WO 99/02185, published Jan. 21, 1999; International Patent Publication No. WO 01/82944, published Nov. 8, 2001; U.S. Pat. Nos.: 5,891,994; 6,193,981; 6,399,067; 6,524,582; and 6,525,179; US Published Patent Application Nos. US 2003/0,166,832 and US 2003/0,180,326) refer to antibodies to certain epitopes on HIV-1 Tat protein as AIDS vaccine and therapeutic agents.

For example, these publications refer to antibodies which specifically bind to an epitope located within the "HIV-1 Tat Epitope 1" sequence spanning Tat amino acid residues 4-12, as follows: Val-Asp-Pro-$X_7$-Leu-$Y_9$-Pro-Trp-$Z_{12}$- SEQ ID NO: 1, wherein $X_7$ is Arg, Lys, Ser or Asn, $Y_9$ is Glu or Asp, and $Z_{12}$ is Lys or Asn, and compositions combining this antibody with other antibodies to HIV-1 Tat. These publications also refer to another antibody composition containing isolated antibodies which bind specifically to an epitope located within the "HIV-1 Tat Epitope 2" sequence spanning Tat amino acid residues 41-50 of the formula -Lys-$X_{42}$-Leu-Gly-Ile-Ser-Tyr-Gly-Arg-Lys- SEQ ID NO: 2, where $X_{42}$ is Gly or Ala. Additionally, these publications refer to isolated antibodies which bind specifically to an epitope located within the "HIV-1 Tat Epitope 3" sequence spanning Tat amino acid residues 56-62 of the formula -Arg-Arg-$X_{58}$-$Z_{59}$-$A_{60}$-$Y_{61}$-Ser- SEQ ID NO: 3, wherein $X_{58}$ is Ala, Pro, Ser, or Gln, $Z_{59}$ is Pro or His, $A_{60}$ is Gln or Pro, and $Y_{61}$ is Asp, Asn, Gly or Ser, or to an epitope located within the "HIV-1 Tat Epitope 4" sequence spanning Tat amino acid residues 62-73 of the formula -Ser-Gln-$X_{64}$-His-Gln-$Y_{67}$-Ser-Leu-Ser-Lys-Gln-Pro- SEQ ID NO: 4, wherein $X_{64}$ is Asn or Thr, and $Y_{67}$ is Ala or Val.

Compositions formed of combinations of these antibodies, particularly combinations of an antibody to one Epitope 1 variant with one or more antibodies that each binds a different Epitope 1 variant, and further combinations of such Epitope 1 antibodies and Epitope 2 antibodies, among other combinations are able to bind a large number of Tat variant sequences characteristic of the multiple strains and subtypes of HIV-1, both B and non-B clades. These antibody compositions are designed to inhibit HIV-1 infectivity during initial infection and/or lower viral load post sero-conversion, thus delaying progression to AIDS. Further, these resulting compositions or mixtures of such anti-Tat antibodies are advantageous as treatments for many strains and subtypes of the virus, thus obviating the need for different, and strain-specific, therapeutic agents.

Despite the growing knowledge about HIV-1 disease progression, there remains a need in the art for the development of compositions and methods for treatment of chronic infection with HIV-1, to retard or prevent progression of the infection to the generally fatal, full-blown AIDS.

SUMMARY OF THE INVENTION

In one aspect, the invention provides a single isolated antibody or fragment thereof, which binds to multiple HIV-1 Tat Epitope 1 variant sequences (hereafter referred to as a "pan-Epitope 1" antibody) and thereby binds to HIV-1 Tat protein from multiple strains and subtypes. In one embodiment, the single pan-Epitope 1 antibody binds to five or at least five variant sequences of HIV-1 Tat Epitope 1, which is specifically defined in the following detailed description of the invention.

In another embodiment, the single pan-Epitope 1 antibody binds to at least two variant sequences of HIV-1 Tat Epitope 1. In yet another embodiment, the single pan-Epitope 1 antibody or fragment binds at least one of the variant Tat Epitope 1 sequences (a) through (d) as defined below and at least one of the variant sequences (e) through (h) as defined below. In another embodiment, the single pan-Epitope 1 antibody binds to at least three, or at least four, of the variant HIV-1 Tat Epitope 1 sequences.

In another embodiment, the single pan-Epitope 1 antibody binds to at least six, of these sequences. In another embodiment, the single pan-Epitope 1 antibody binds to at least seven, or at least eight, of the variant HIV-1 Tat Epitope 1 sequences. In another embodiment, the single pan-Epitope 1 antibody binds to nine or more variant HIV-1 Tat Epitope 1 sequences. In another embodiment, a single pan-Epitope 1 antibody is reactive with greater than 95% of the known variants of the HIV-1 Tat protein (both B and non-B clades).

In another aspect, the invention provides a pharmaceutical composition comprising one single pan-Epitope 1 antibody as above defined. In another embodiment, the composition contains multiple different pan-Epitope 1 antibodies as above-defined. In still a further embodiment, the composition contains an additional antibody to HIV-1. Such a composition is intended to minimize chronic viremia which leads to AIDS. Such a composition is useful for chronically infected, symptomatic or asympomatic patients, or for patients on other anti-retroviral treatments.

In still a further aspect, the invention provides a diagnostic assay reagent comprising a single pan-Epitope 1 antibody or fragment as above-defined and a detectable label or label system.

In another aspect, the invention provides a kit for use in performing a sandwich assay comprising one or more pan-Epitope 1 antibodies or fragments, one or more additional antibody to HIV-1 Tat which binds to an epitope on HIV-1 Tat other than Epitope 1, and optionally one or more detectable labels or label systems for identifying binding of the antibodies.

In another aspect, the invention provides a kit for use in performing an assay comprising one or more pan-Epitope 1 antibodies or fragments and one or more detectable labels or label systems for identifying binding of the pan-Epitope 1 antibody to the Tat. Either kit of the invention also includes coated solid supports, miscellaneous substrates and apparatus for evoking or detecting the signals provided by the labels, as well as conventional apparatus for taking blood samples, appropriate vials and other diagnostic assay components.

In still a further aspect, the invention provides a method of inhibiting replication of HIV-1 or reducing the viral levels of HIV-1 in an infected human subject by administering to said subject a pharmaceutical composition as defined herein. In one embodiment the method involves administering the compositions of this invention to maintain lower viral levels of HIV-1 in a chronically infected subject.

In another aspect, the invention provides the use of a pan-Epitope 1 antibody in the preparation of a medicament for inhibiting replication of HIV-1 in a human subject. In one embodiment, this use employs a pan-Epitope 1 antibody that binds five or more different Epitope 1 variant sequences. In another aspect the invention provides the use of a pan-Epitope 1 antibody or antibody fragment and an anti-Epitope 2 antibody or antibody fragment in the preparation of a medicament for inhibiting replication of HIV-1 in a human subject.

In a further aspect, the invention provides a method of making a single isolated pan-Epitope 1 antibody or fragment thereof.

In still another aspect, the invention provides a diagnostic assay to measure levels of HIV-1 Tat in a subject. In one embodiment, the assay is a competition assay employing a pan-Epitope 1 antibody of this invention. In a further embodiment, the pan-Epitope 1 antibody is one that binds at least five of the Tat Epitope 1 variant sequences, i.e., pan-Epitope 1 antibody #5.

Other aspects and advantages of the present invention are described further in the following detailed description of the preferred embodiments thereof.

DETAILED DESCRIPTION OF THE INVENTION

Figure 1:
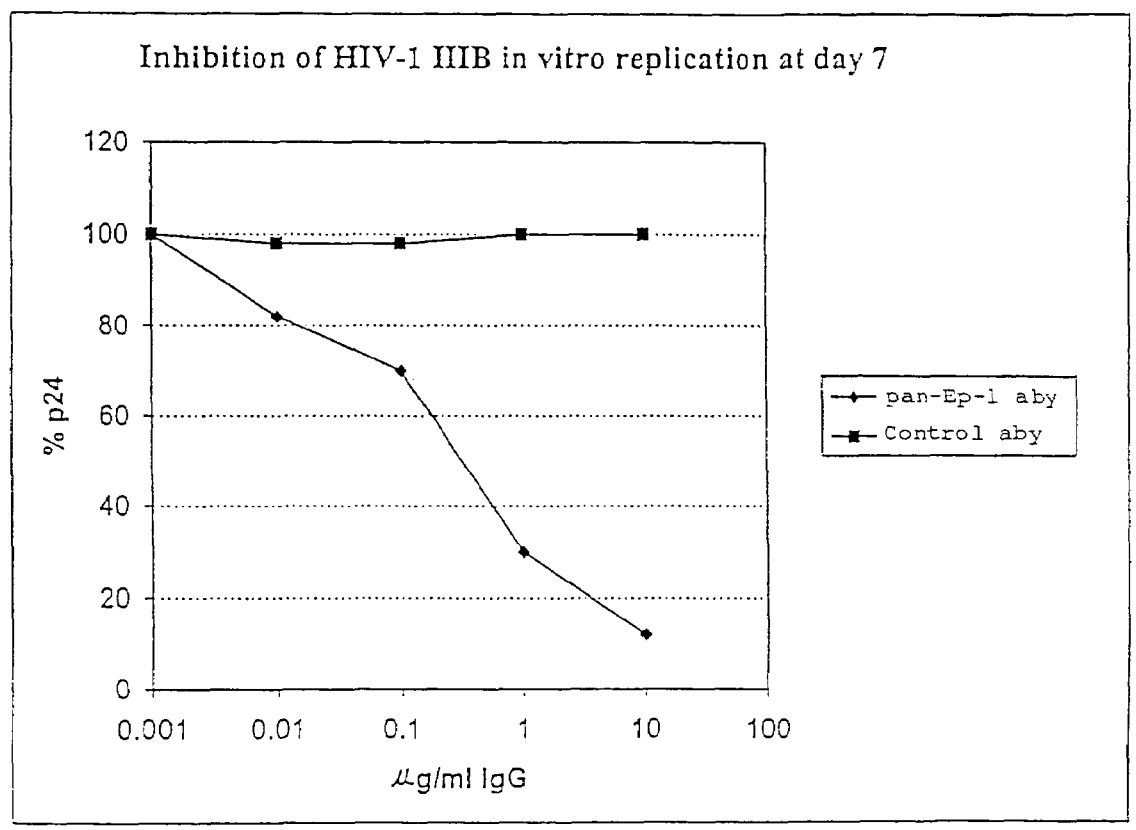
FIG. 1 is a graph plotting inhibition of HIV-1 strain IIIb replication in HIV-1-infected (1% initial infection) Jurkat cells exposed to increasing concentrations (μg/ml) of a pan-Epitope 1 IgG antibody of the invention (pan-Ep-1 aby, diamond) compared to an antibody control (square). The pan-Epitope 1 IgG antibody binds five variants of the HIV-1 Tat Epitope 1. These five variants would be present in greater than 95% of the HIV-1 B and non-B strains of the virus. Virus levels were determined through a HIV-1 p24 protein-detecting ELISA at day 7 post infection. The data show inhibition with increasing antibody concentration vs. the control.

This invention addresses the need in the art for therapeutic and diagnostic reagents and compositions for use in treating and diagnosing HIV-1 infection of multiple strains and subtypes. One unique advantage of the pan-Epitope 1 compositions of this invention involves the formulation and application of therapies that are less complex, that use a smaller number of reagents, and yet are efficacious against a full range of HIV-1 strains and subtypes. Similarly, the present invention permits detection of multiple HIV-1 strains and subtypes with a single assay and minimum number of reagents, thereby obviating multiple separate tests and reagents for each strain or subtype of HIV-1 by which a subject may be infected.

HIV-1 Tat Epitope 1 and the Pan-Epitope 1 Antibody

As used herein, the term "variant HIV-1 Tat Epitope 1 sequences" refers to the sequences represented by the formula $R_1$-Asp-Pro-$X_7$-Leu-$Y_9$-Pro-$R_2$ SEQ ID NO: 5, wherein $X_7$ is Arg, Lys, Ser or Asn; $Y_9$ is Glu or Asp; $R_1$ is absent, Val, Glu-Val, or Glu-Pro-Val; and $R_2$ is absent or Trp-$Z_{12}$-$R_3$, wherein $Z_{12}$ is absent, Lys, or Asn, and $R_3$ is absent or is all or part of the sequence -His-Pro-Gly-Ser- SEQ ID NO: 27. According to one preferred embodiment, an Epitope 1 sequence contains variable amino acids at the $X_7$ and $Y_9$ positions and $R_1$ as Val and $R_2$ is absent, i.e., Val-Asp-Pro-$X_7$-Leu-$Y_9$-Pro SEQ ID NO: 28. According to another embodiment an Epitope 1 sequence contains the three variable positions, $X_7$, $Y_9$ and $Z_{12}$ positions, an absent $R_1$, and an $R_2$ which is Trp-$Z_{12}$-$R_3$, wherein $R_3$ is absent, e.g., Asp-Pro-$X_7$-Leu-$Y_9$-Pro-Trp-$Z_{12}$ SEQ ID NO: 29. Given the above formula, the entire scope of variant Epitope 1 sequences may be sequences of between 7 and about 14 amino acids in length, either containing fragments of the above-identified SEQ ID NO: 5 or larger sequences encompassing the fragments or entirety of SEQ ID NO: 5. Thus there exist greater than the eight Epitope 1 variant sequences specified by the Examples below.

As another embodiment, other variant HIV-1 Tat Epitope 1 sequences include the sequences represented by the formula Glu-Val-Asp-Pro-$X_7$-Leu-$Y_9$-Pro SEQ ID NO: 30, Val-Asp-Pro-$X_7$-Leu-$Y_9$-Trp-$Z_{12}$- SEQ ID NO: 31, and Val-Asp-Pro-$X_7$-Leu-$Y_9$-Trp-$Z_{12}$-His-Pro-Gly-Ser- SEQ ID NO: 32, as well as other sequences falling within the above formula. In one embodiment, exemplified below, certain selected variant HIV-1 Epitope 1 sequences are represented by the following eight sequences:

(a) -Val-Asp-Pro-Arg-Leu-Glu-Pro-  SEQ ID NO: 33
(b) -Val-Asp-Pro-Lys-Leu-Glu-Pro-  SEQ ID NO: 34
(c) -Val-Asp-Pro-Ser-Leu-Glu-Pro-  SEQ ID NO: 35
(d) -Val-Asp-Pro-Asn-Leu-Glu-Pro-  SEQ ID NO: 36
(e) -Val-Asp-Pro-Arg-Leu-Asp-Pro-  SEQ ID NO: 37
(f) -Val-Asp-Pro-Lys-Leu-Asp-Pro-  SEQ ID NO: 38
(g) -Val-Asp-Pro-Ser-Leu-Asp-Pro-  SEQ ID NO: 39
(h) -Val-Asp-Pro-Asn-Leu-Asp-Pro-  SEQ ID NO: 40

Thus, in one embodiment, for example, a pan-Epitope 1 antibody binds to variants (a), (b), (c), (d), and (h). In another embodiment a pan-Epitope 1 antibody binds to different combinations of multiple variants of (a) through (h).

This definition of Epitope 1 also encompasses homologous or analogous modified epitope sequences, wherein the non-variable amino acids in the formula of SEQ ID NO: 5 (i.e., those not represented by a single letter and subscript) may be conservatively replaced individually by amino acid residues having similar characteristics. For example, the non-variable amino acid residues of SEQ ID NO: 5 may be replaced by other amino acid residues bearing the same charge and/or similar side chain lengths. Similarly the non-variable naturally-occurring amino acids in the SEQ ID NO: 5 may be replaced by unnatural amino acid residues, i.e., an amino acid having a modification in the chemical structure, e.g., a D-amino acid, an amino acid bearing a non-naturally occurring side chains an N-methylated amino acid, etc. See, the cited references relating to N-methylated amino acids, among others. See, e.g., L. Aurelio et al, 2002 Organic Letters, 4(21): 3767-3769 and references cited therein.

Thus the present invention provides a "pan-Epitope 1 antibody", which term refers to a single, isolated antibody or fragment thereof that is capable of binding to multiple HIV-1 Epitope 1 amino acid sequences. Desirably, as demonstrated in the examples below, the pan-Epitope 1 antibody has a $K_D$ of $1.0 \times 10^{-9}$ or less for all variant sequences to which it binds. One of skill in the art will readily understand that the dissociation constant $K_D$ is derived from the measures of association ($k_a$) and dissociation ($k_d$). All pan-Epitope 1 antibodies of this invention desirably have similar $K_D$ values.

As exemplified herein, one embodiment of a pan-Epitope 1 antibody is a single isolated antibody or fragment that is capable of binding to at least five variant HIV-1 Epitope 1 sequences. In a further embodiment, the pan-Epitope 1 antibody is a single isolated antibody or fragment that is capable of binding to five variant HIV-1 Epitope 1 sequences. In still a further embodiment, the pan-Epitope 1 antibody is a single isolated antibody or fragment that is capable of binding to the following five variant HIV-1 Epitope 1 amino acid sequences: VDPRLEPW-$Z_{12}$-$R_3$ (SEQ ID NO: 6); VDPKLEPW-$Z_{12}$-$R_3$ (SEQ ID NO: 7); VDPSLEPW-$Z_{12}$-$R_3$ (SEQ ID NO: 8); VDPNLEPW-$Z_{12}$-$R_3$ (SEQ ID NO: 9); and VDPNLDPW-$Z_{12}$-$R_3$ (SEQ ID NO: 10), wherein $Z_{12}$ is Lys or Asn, and $R_3$ is absent or all or part of the sequence -His-Pro-Gly-Ser- SEQ ID NO: 27. This exemplified IgG1 pan-Epitope 1 antibody that binds to five variants is shown in the assays below to have a $K_D$ of $1.0 \times 10^{-9}$ or less for all five variant sequences.

Another embodiment of a pan-Epitope 1 antibody is a single, isolated antibody or fragment thereof that is capable of binding to at least two variant HIV-1 Epitope 1 sequences, such as two of the above-listed variant Epitope 1 sequences (a) through (h). Still another embodiment of a pan-Epitope 1 antibody is a single, isolated antibody or fragment thereof that is capable of binding to at least three variant HIV-1 Epitope 1 sequences. Another embodiment of a pan-Epitope 1 antibody is a single, isolated antibody or fragment thereof that is capable of binding to at least four variant HIV-1 Epitope 1 sequences. In another embodiment, the pan-Epitope 1 antibody of the invention which binds to from two to four different Epitope 1 variants is an antibody or fragment that binds to at least one variant HIV-1 Epitope 1 sequence having Glu in position $Y_9$ and at least one variant HIV-1 Epitope 1 sequence having Asp in position $Y_9$.

In another embodiment, a single, isolated antibody or fragment that is a pan-Epitope 1 antibody binds to at least six variant HIV-1 Epitope 1 sequences. An additional embodiment includes a single, isolated antibody or fragment thereof that is capable of binding to at least seven variant HIV-1 Epitope 1 sequences. That term also refers to a single, isolated antibody or fragment thereof that is capable of binding to at least eight variant HIV-1 Epitope 1 sequences. That term also refers to a single, isolated antibody or fragment thereof that is capable of binding to at least nine or more variant HIV-1 Epitope 1 sequences, when the additional variable positions of $Z_{12}$ or any flanking amino acids are taken into account. In still further embodiments, as demonstrated in the examples below, the pan-Epitope 1 antibody has a $K_D$ of $1.0 \times 10^{-9}$ or less for each variant sequence.

In one embodiment, as taught in detail in the Examples below, a single selected pan-Epitope 1 antibody binds from two up to eight of the variant HIV-1 Epitope 1 sequences represented by the aforementioned eight sequences (a) through (h).

Thus, one single isolated pan-Epitope 1 antibody or fragment binds at least two of the variant sequences (a) through (h). Another single isolated antibody or fragment of the invention binds to from two to four said different variant sequences. A specific embodiment of such a single isolated pan-Epitope 1 antibody or fragment binds at least one of said variant sequences (a) through (d) and at least one of said variant sequences (e) through (h). Still other single isolated pan-Epitope 1 antibody or fragment binds any five through all eight of the variant sequences (a) through (h). As exemplified below, the pan-Epitope 1 antibody generated from one specific clone binds 5 variants of Epitope 1 (a) through (d), and (h). This specific antibody is referred throughout this specification as pan-Epitope antibody #5.

However, as noted above, other examples of pan-Epitope 1 antibodies may bind other Epitope 1 sequences, containing the $Z_{12}$ amino acid or homologous sequences represented by (a) through (h) above in which at least one non-variable amino acid is an unnatural amino acid.

Thus, a single pan-Epitope antibody or fragment of the present invention binds to HIV-1 Tat protein from multiple strains and subtypes. In one embodiment, a single pan-Epitope antibody or fragment binds to greater than 95% of the known HIV-1 strains and subtypes, including strains and subtypes from both B and non-B clades.

As used herein, the term "antibody" refers to an intact immunoglobulin having two light and two heavy chains. Thus a single isolated antibody or fragment may be a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, an Fv construct, a Fab construct, an Fc construct, a light chain variable or complementarity determining region (CDR) sequence, etc.

Such pan-Epitope 1 antibodies or fragments are generated using sequential selection and screening techniques such as described in the Examples below or using other synthetic or recombinant techniques. As referred to above, the single isolated pan-Epitope 1 antibody or fragment of this invention may be prepared by a method involving serial and sequential selection and screening from libraries of antibodies or antibody fragments. For example, selections involve contacting each single chain human Fv library with a synthetic Epitope 1 peptide and/or recombinant Tat protein, and presenting variant Tat Epitope 1 sequences to the libraries. For example, a library of single chain antibody variable sequences (scFv) is selected for sequences that bind to a first Epitope 1 variant amino acid sequence, such as a biotinylated peptide containing the variant sequence. A mixture of scFv that bind to this first sequence is obtained and the scFv that do not bind are discarded from the library. The resulting selected scFv mixture is then again serially and sequentially contacted with as many different Epitope 1 sequences as desired and the non-binding scFv successively discarded, until a mixture of resulting scFv is obtained that bind multiple variants of Epitope 1, e.g., from two, three, four, five, six, seven or eight or more different sequences of Epitope 1. The resulting scFv that binds to the desired number of Epitope 1 variants is then manipulated and cloned to provide source of that selected scFv. For example, the scFV is manipulated to present it in the antibody or fragment form desired.

Thereafter each clone is screened to determine its reactivity to different HIV-1 Tat Epitope 1 variants of different HIV-1 strains and subtypes. The screen is expanded until an antibody or antibody fragment or construct is obtained which exhibits the required binding to the selected multiple variant sequences, e.g., two, three, four, five, six, seven or eight or more Epitope 1 variant sequences of SEQ ID NO: 5.

The pan-Epitope 1 antibody must contain variable regions from the scFv that are capable of mediating binding to the multiple Epitope 1 variants. However, the constant regions can be altered by now conventional means. For example, the variable region of each pan-Epitope 1 scFv may be inserted into a constant region backbone, such as a human IgG1 backbone. Such an antibody is described in Example 1 below. Thus the resulting pan-Epitope 1 antibody may be a chimeric antibody containing human light chain variable regions associated with heavy chains from human or non-human sources, e.g., monkeys, etc., or a humanized antibody, using human IgG antibody backbones, or an antibody fragment. Selection of a suitable antibody backbone and insertion of the pan-Epitope 1 scFv are within the skill of the art, provided with this specification and the conventional teachings of immunology.

Given the teachings of this specification, one of skill in the art may generate any the different pan-Epitope 1 antibodies described herein.

Pharmaceutical Compositions and Methods of the Invention

Thus, another aspect of this invention is a pharmaceutical composition useful for the treatment of HIV-1 that contains a pan-Epitope 1 antibody or fragment and a pharmaceutically acceptable carrier. Such a pharmaceutical composition may preferably contain a single pan-Epitope 1 antibody or fragment that binds eight $X_7/Y_9$ variants of the Epitope 1 formula. Another pharmaceutical composition may contain a single pan-Epitope 1 antibody or fragment that binds five or more of the $X_7/Y_9$ variants of the Epitope 1. Still another pharmaceutical composition may contain a single pan-Epitope 1 antibody or fragment that binds two through seven of the $X_7/Y_9$ variants of Epitope 1. Yet another composition can contain a single pan-Epitope 1 antibody or fragment that binds nine or more $X_7/Y_9/Z_{12}$ variants of Epitope 1.

Additional embodiments of pharmaceutical compositions may contain two or more different pan-Epitope 1 antibodies of this invention, e.g., two or three antibodies that each bind multiple different variants. For example, one pan-Epitope 1 antibody in a composition may bind only Epitope 1 variants in which $Y_9$ is Glu and the second Epitope 1 antibody in the composition binds only the variants in which $Y_9$ is Asp. A variety of such combinations may be readily prepared by one of skill in the art given this disclosure.

Pharmaceutical compositions of this invention also may contain antibodies to other HIV-1 epitopes, such as the previously identified HIV-1 Tat Epitope 2. As used herein, the term "HIV-1 Tat Epitope 2" refers to the sequence -Lys-$X_{42}$-Leu-Gly-Ile-Ser-Tyr-Gly-Arg-Lys- SEQ ID NO: 2, where $X_{42}$ is Gly or Ala.

Thus, one pharmaceutical composition may contain a pan-Epitope 1 antibody of this invention in combination with an antibody the specifically binds an epitope sequence located within Epitope 2.

Still other antibodies to other proteins and immunogenic sites on the HIV-1 virus may be readily generated and combined in a suitable pharmaceutical composition of this invention. Alternatively, the compositions of this invention may be used in conjunction with, or sequentially with, other HIV-1 anti-viral therapies or pharmaceutical regimens.

As defined herein, the pharmaceutically acceptable carrier suitable for use in an immunogenic proteinaceous composition of the invention are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents, inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, $4^{th}$ edit., eds. R. C. Rowe et al, APhA Publications, 2003.

Thus the invention provides for use of a pan-Epitope 1 antibody in the preparation of a medicament for inhibiting replication of HIV-1 in a human subject.

Such pharmaceutical compositions of this invention are useful in a method of inhibiting replication of HIV-1 in a human subject exposed to HIV-1. A suitable dose of a composition according to this invention is administered to a human subject in an amount effective to bind HIV-1 Tat protein released from infected cells. In one embodiment, the pharmaceutical compositions may be therapeutically administered to an HIV-1 infected human for treatment or control of viral infection. Such an infected human may be asymptomatic or symptomatic. The pan-Epitope 1 antibodies reduce chronic viral multiplication in infected subjects and minimize progression to AIDS. See, e.g., the in vitro results of an inhibition assay embodied in the previously-discussed FIG. 1.

The method operates by permitting the pan-Epitope 1 antibody to block the transfer of Tat from infected cells to other infected or uninfected cells. This action reduces the multiplicity of infection and blocks the burst of HIV-1 viral expansion, and thus lowers viral levels. In already infected patients, this method of reduction of viral levels can reduce chronic viremia and progression to AIDS. The method can involve chronically administering the composition. Among such patients suitable for treatment with this method are HIV-1 infected patients who are immunocompromised by disease and unable to mount a strong immune response. In later stages of HIV infection, the likelihood of generating effective titers of antibodies is less, due to the immune impairment associated with the disease. Also among such patients are HIV-1 infected pregnant women, neonates of infected mothers, and unimmunized patients with putative exposure (e.g., a human who has been inadvertently "stuck" with a needle used by an HIV-1 infected human).

These pan-Epitope 1 antibody compositions are administered as passive immunotherapy to inhibit viral multiplication and lower the viral load. The exogenous antibodies which react with greater than 95%, or greater than 99%, of known Tat proteins from HIV-1 provide in the patient an immediate interdiction of the transfer of Tat from virally infected cells to other infected or uninfected cells. According to this method, the patient may be chronically treated with the antibody composition for a long treatment regimen.

Another unique aspect of the present invention is provided by an alternative method of inhibiting HIV-1 replication, which involves administering both the pan-Epitope 1 antibody and an Epitope 2 antibody to an infected patient. It is anticipated that such a method may employ administering a combination of pan-Epitope 1 antibody and an Epitope 2 antibody as a single composition. Alternatively, each antibody may be administered as a separate composition, in conjunction or sequentially to the patient. Surprisingly the combination of the two antibodies or antibody fragments produces a synergistic result. This result indicates that when administered used together, dosages of the antibodies that are lower than the dosages used when each antibody is administered separately are useful to achieve the desired therapeutic result, i.e., a reduction in viremia.

The synergy between these two reagents is exemplified in an inhibition assay. When used in an in vitro inhibition assay format for the inhibition of HIV-1 Tat levels in HIV-1 infected cell culture, the pan-Epitope 1 antibody and the Epitope 2 antibody, used alone as a pharmaceutical composition, produce parallel virus-inhibiting results. See, e.g., FIG. 2. However, unexpectedly the two antibodies, administered together, provide a more potent inhibition of virus levels than the relatively equivalent inhibition provided when either anti-Tat antibody is used alone. See, the results of the assay described for FIG. 2. Such synergistic activity of the pan-Epitope 1 antibody with an Epitope 2 antibody was not expected.

In each of the above-described methods, these compositions of the present invention are administered by an appropriate route, e.g., by the subcutaneous, oral, mucosal, intravenous, intraperitoneal, intramuscular, nasal, or inhalation routes. The presently preferred route of administration is subcutaneous, intravenous or intramuscular.

The amount of the pan-Epitope 1 antibody of the invention, with or without other anti-HIV-1 antibodies present in each dose, is selected with regard to consideration of the patient's age, weight, sex, general physical condition and the like. The amount of antibody required to produce an exogenous effect in the patient without significant adverse side effects varies depending upon the pharmaceutical composition employed. In infected patients, generally, each dose will comprise between about 5 to 400 mg/mL injection of the pan-Epitope 1 antibody in a sterile solution. Another dosage is about 200 mg of the antibody. Still another dosage is about 100 mg of the antibody. Still another embodiment is a dosage of about 50 mg of the antibody. A further embodiment is a dosage of about 10 mg of the antibody. When used together, dosages of the pan-Epitope 1 antibody and an Epitope 2 antibody, in one embodiment, are the same as above. In another embodiment, due to the synergy between the two antibodies, a combination dosage is lower than additive single dosages of each antibody alone.

The frequency of chronic administration may range from daily dosages to once or twice a week to once a month, and may depend upon the half-life of the antibody (e.g., about 7-21 days). However, the duration of chronic treatment for such infected patients is anticipated to be an indefinite, but prolonged period. Other dosage ranges may also be contemplated by one of skill in the art, particularly where administration of the antibody composition is in conjunction or sequential with other anti-viral treatments.

The compositions of the present invention can be employed in chronic treatments for subjects at risk of acute infection due to needle sticks or maternal infection. The antibody compositions of the present invention can also be employed in chronic treatments for infected patients, or patients with advanced HIV.

Diagnostic Reagents, Kits and Assays of the Invention

As additional embodiment of this invention, the pan-Epitope 1 antibody or fragment of this invention is useful as a diagnostic assay reagent, and may be used with a detectable label or label system, or be immobilized on a substrate, or be associated with another agent that mediates immobilization.

Such a diagnostic reagent may contain a single pan-Epitope 1 antibody or fragment that binds eight $X_7/Y_9$ variants of the Epitope 1 formula. Another diagnostic reagent may contain a single pan-Epitope 1 antibody or fragment that binds five or more of the $X_7/Y_9$ variants of the Epitope 1. Still another diagnostic reagent may contain a single pan-Epitope 1 antibody or fragment that binds two through eight of the $X_7/Y_9$ variants of Epitope 1. Yet another diagnostic reagent can contain a single pan-Epitope 1 antibody or fragment that binds nine or more $X_7/Y_9/Z_{12}$ variants of Epitope 1.

Still another embodiment of this invention includes diagnostic kits of this invention which may contain a single pan-Epitope 1 antibody of this invention, or several different pan-Epitope 1 antibodies of this invention. For example, one pan-Epitope 1 antibody in a reagent may bind only Epitope 1 variants in which $Y_9$ is Glu and the second Epitope 1 antibody in the reagent binds only the variants in which $Y_9$ is Asp. A variety of such combinations may be readily prepared by one of skill in the art given this disclosure. Such diagnostic or assay kits may also contain antibodies to other HIV-1 epitopes or non-Tat proteins.

Such kits and reagents are useful for the measurement and detection of titers of HIV-1 and HIV-1 Tat in a subject infected with HIV-1 or possibly so infected. The antibodies may be immobilized on suitable substrates, e.g., bound to an avidin-coated solid support, e.g., plates, sticks, or beads. Of course, other binding agents known to those of skill in the diagnostic assay art may also be employed for the same purposes.

Also provided in the kit are reagents which detect the binding of antibody to the HIV-1 Tat, such as a non-human antibody, e.g., goat anti-human immunoglobulin, or the like. Other reagents include conventional diagnostic labels or label systems. For example, the antibodies may be labeled directly or indirectly, with, e.g., radioactive compounds, radioisotopes, such as $^{32}P$, $^{125}I$, tecnicium; fluorescent or chemiluminescent compounds, such as FITC, rhodamine or luciferin; and proteins such as biotin or enzymes and enzyme co-factors, such as alkaline phosphatase, beta-glactosidase or horseradish peroxidase; and/or molecular labels such as FLAG, etc. See, e.g., Chubet R G, Brizzard B L. 1996 Biotechniques 20(1):136-141; and Knappik A, Pluckthun A. 1994 Biotechniques 1994;17(4):754-761. Other elements of the label systems include substrates useful for generating the signals upon interaction with the other components of the label system, e.g., a streptavidin and horseradish peroxidase system. Any method known in the art for separately conjugating the antibody to the detectable moiety may be employed, including those methods described by Hunter, et al, 1962 Nature 133: 945; Pain et al 1981 J. Immunol., Meth. 40:219 and other conventional texts.

Alternatively, the labels may be used apart from the antibodies. The kit thus also contains miscellaneous reagents and apparatus for reading labels, e.g., certain substrates that interact with an enzymatic label to produce a color signal, etc., apparatus for taking blood samples, as well as appropriate vials and other diagnostic assay components.

The antibodies of the present invention may be employed in any known assay method, such as competitive binding assays, direct and indirect sandwich assays, and immunoprecipitation assays. See, e.g., Zola, Monoclonal Antibodies: A Manual of Techniques, pp 147-158 (CRC Press, Inc. 1987) and other conventional assay texts for a variety of assay protocols. As one embodiment, a kit for use in detecting HIV-1 Tat levels in patients may contain one or more pan-Epitope 1 antibodies or fragments, one or more optional additional antibody to HIV-1 Tat which binds to an epitope on HIV-1 Tat that is different from an Epitope 1 sequence; and one or more detectable labels or label systems for identifying binding of these antibodies. One of skill in the art may also readily select other conventional diagnostic components for this kit.

In another embodiment, a kit for use in detecting HIV-1 Tat levels in patients contains a single pan-Epitope 1 antibody or fragment, or alternatively multiple pan-Epitope 1 antibodies and fragments, and one or more detectable labels or label systems for identifying binding of these antibodies. Such a kit is suitable for use in the practice of a competition assay.

Such kits and reagents may be employed in a variety of assay formats for assessing the titer of HIV-1 in a patient. Such a patient may be uninfected, infected or undergoing treatment with the pharmaceutical compositions of this invention or other anti-HIV-1 therapeutics.

In one embodiment of the invention, the pan-Epitope 1 antibody additionally permits the use of a competition assay. In this embodiment, a diagnostic assay to measure levels of HIV-1 Tat in a subject includes contacting a substrate on which is immobilized a known amount of HIV-1 Tat protein with a biological sample from a subject containing an unknown amount of HIV-1 Tat and a single isolated pan-Epitope 1 antibody or fragment of this invention that is associated with a detectable label. The pan-Epitope 1 antibody or fragment is present at a subsaturation amount relative to the known amount of bound Tat on the substrate. The substrate is rinsed and the amount of the pan-Epitope antibody or fragment bound to said substrate is measured.

The amount of bound pan-Epitope 1 antibody is compared to a standard binding curve measuring the binding of various known amounts of that pan-Epitope 1 antibody or fragment to said known amount of bound Tat in the absence of said sample. Thus, the amount of Tat in said sample is indicated by an inverse relationship to the amount of said antibody bound to said substrate.

This competition assay employing a pan-Epitope 1 antibody or fragment binds between 2-8, i.e., 2, 3, 4, 5, 6, 7, or 8, or an even greater number of Epitope 1 variant sequences and permits a simple, more efficient assay. The single reagent assay of this invention enables the detection of HIV-1 infection of multiple strains and subtypes without the need for multiple reagents and multiple assays.

For example, another embodiment of a diagnostic assay to measure levels of HIV-1 Tat involves contacting a biological sample from a subject, e.g., a body fluid, preferably blood, serum or plasma, but also possibly urine, saliva and other fluids or tissue, with an immobilized "capture" antibody that binds HIV-1 Tat in a sample. The immobilized capture antibody may be either a pan-Epitope 1 antibody or an antibody that binds an epitope of HIV-1 Tat that is different from the Epitope 1.

Immobilization is provided by binding the capture antibody to a solid support, such as a plate, strip or beads. Once the biological sample is exposed to the immobilized antibody for a sufficient time, the support is washed to eliminate any material from the biological sample which is not bound to the peptides. Such washing steps are conventional in diagnostic assays, and performed with conventional buffers.

If HIV-1 Tat protein is present in the sample, that Tat will be immobilized by binding to the bound capture antibody. Thereafter, the bound material is contacted with a second "detector" antibody to HIV-1 Tat. The detector antibody may be a pan-Epitope 1 antibody or an antibody that binds an epitope of HIV-1 Tat that is different from the Epitope 1, or a different species non-human antibody, provided that the detector antibody is different from the capture antibody. The detector antibody binds to a different epitope on the bound HIV-1 Tat than the capture antibody and thus permits detection of the binding between the capture antibody on the solid support and HIV-1 Tat in the biological sample.

The second detector antibody may be labeled with a detectable label or a component capable of producing a detectable signal, e.g., biotinylated or the antibody may contain an molecular tag, e.g., FLAG. Alternatively, the label may not be part of the antibody. Suitable labels are selected from among a wide array of conventionally employed diagnostic labels, as discussed above. In one embodiment, the label can be an enzyme, which upon contact with a substrate, produces a detectable color or chemiluminescent signal. The presence and/or intensity of the color or chemiluminescence provides evidence of the amount of Tat in the sample.

Any conventional assay employing the antibodies of this invention may be employed to determine the efficacy of therapeutic treatment, as well as original diagnosis of disease.

The following examples illustrate certain embodiments of the compositions and methods of this invention. These examples do not limit the disclosure of the claims and specification.

EXAMPLES

Example 1

Selection and Screening Processes to Produce Pan-Epitope 1 Antibody IgG

A. Peptides

Throughout the following example, amino acids are represented by the well-known single letter code. Peptides used in the following examples are identified in Table 1 below. These peptides were synthesized with Biotin-Ser-Gly-Ser-Gly- (SEQ ID NO: 11) at the N-terminus. That N-terminal sequence serves as a spacer to ensure that the relevant peptide sequence is external to the biotin binding pocket of avidin. The presence of the Ser in the typical $Z_{12}$ position in certain of the exemplary peptide sequences was also provided as a spacer and was a substitution for the position $Z_{12}$.

The amino acid residues at the variable positions $X_7$ and $Y_9$ of Epitope 1 are in bold in the table.

TABLE 1

| Peptide name | Peptides/Proteins (Bio indicates biotinylation) | SEQ ID NO |
|---|---|---|
| WHOLE TAT | [1]MEPVDPRLEP WKHPGSQPKT ACTNCYCKKC CFHCQVCFIT KALGISYGRK KRRQRRRPPQ GSQTHQVSLS KQPTSQSRGD PTGPKE[86] | 12 |
| E2-bio | Bio-SGSG-LGISYGRKS | 13 |
| E1-RE | Bio-SGSG-VDPRLEPW | 14 |
| E1-KE | Bio-SGSG-VDPKLEPW | 15 |
| E1-NE | Bio-SGSG-VDPNLEPW | 16 |
| E1-SE | Bio-SGSG-VDPSLEPW | 17 |
| E1-RD | Bio-SGSG-VDPRLDPW | 18 |
| E1-KD | Bio-SGSG-VDPKLDPW | 19 |
| E1-SD | Bio-SGSG-VDPSLDPW | 20 |
| E1-ND | Bio-SGSG-VDPNLDPW | 21 |
| E1-RE (alt) | Bio-SGSG-EPVDPRLEPWS* | 22 |
| E1-KE (alt) | Bio-SGSG-EPVDPKLEPWS* | 23 |
| E1-SE (alt) | Bio-SGSG-EPVDPSLEPWS* | 24 |
| E1-NE (alt) | Bio-SGSG-EPVDPNLEPWS* | 25 |
| E1-ND (alt) | Bio-SGSG-EPVDPNLDPWS* | 26 |

*As used herein, both the shorter biotinylated peptides and the longer ("alt") biotinylated peptides yield the same results. Thus, the additional amino acids on the longer peptides were trivial differences that did not affect the antibody binding function of the epitope sequences themselves.

B. Selection of scFv

Clones were selected from the n-CoDeR® Lib-2000 single chain fragment (ScFv) library (BioInvent International AB, Sweden). Selected scFv were screened against peptides presenting variant Epitope 1 sequences and against whole Tat protein, as follows.

In Step One, the biotinylated peptide E1-RE (alt) was captured with streptavidin-coated Dynabead substrate (Dynal A. S., Oslo, Norway), essentially as described in Griffiths A. D. et al EMBO J., 1994, 13, 3245-3260 and Hawkins, R. E., et al., J. Mol. Biol., 1992, 226, 889-896. These published procedures were modified by elution of bound phages with trypsin, as described in Engberg J., et al., Mol. Biotechnology., 1996, 6, 287-310.

Step Two was performed with a mixture of the biotinylated peptides, referred to as E1-NE (alt), E1-KE (alt) and E1-SE (alt). The peptide concentrations ranged from 1-5×10⁻⁸ M in steps one and two. In Step Three, 4×10⁻⁸ M complete Tat protein (aa 1-86, Xeptagen, Italy) was immobilised to a microtiter plate and used for solid phase selection followed by trypsin elution. The amount of phage used was $9.4 \times 10^{12}$, $3.4 \times 10^{11}$ and $1.4 \, 10^{12}$ pfu in the first, second and third selections, respectively.

For phagemid amplification after Steps One and Two, *E. coli* HB101F' cells were grown to $OD_{600}$ 0.5 in Luria-Bertani medium (LB) and infected with eluted phage at +37° C. for 30 min. The incubation was then continued and overnight at +30° C. on a 500 cm² LB-agar plate containing 100 μg/ml ampicillin and 15 μg/ml tetracycline. Colonies were re-suspended in LB medium and grown at +37° C. until they reached $OD_{600}$ 0.5. Colonies were infected with $6 \times 10^9$ pfu of R408/ml helper phage for 30 minutes. Isopropyl-β-D-thiogalactoside (IPTG) was added to a concentration of 100 μM and incubation was continued at +25° C. overnight. For preparation of phagemid DNA after Step Three, the resulting phages were infected as above and grown for 1.5 hours before the medium was changed (LB+15 μg/ml tetracycline+100 μg/ml ampicillin+0.1% glucose). The growth was continued at +30° C. overnight and miniprep was performed with a plasmid miniprep kit (BioRad, 732-6100).

C. Screening of scFv

To allow expression of soluble scFv the gene III coding region was removed, by restriction enzyme digestion, and the resulting vector was transformed into Top10 bacteria. Expressed scFv clones were tested in a Chemiluminescence ELISA against target (mix of the target peptides used in selection step one and two and a control antigen E2-BIO, using β-FLAG detection (SIGMA, A-9469)). It should be noted that screening with the shorter and longer (alt) peptides produces the same results, as each set of short and longer peptides contains the same Epitope 1 variant sequence, i.e., the same X and Y variants.

A total of 590 out of 4271 clones were found positive in the first screening, i.e., such clones were reactive with the target E1-NE (alt). Positive clones were retested in a secondary screening against all four individual peptides, Tat protein (Xeptagen, Italy) and control antigens (E2-BIO and BSA-oxazolone). Of all tested clones, 322 were found to be positive against all four specific peptides E1-RE (alt), E1-KE (alt), E1-SE (alt), and E1-NE (alt) and against Tat protein, but not against controls. 288 of these clones were further analysed by sequencing. In total, 26 clones were found to have distinct patterns of reactivity and hypervariable region sequences and were expressed as scFv in large volumes.

The screening process resulted in scFvs recognizing one to four sequence variants as well as the complete Tat protein. Only clones recognizing Tat protein as well as all the four variants were further processed and tested against a fifth variant, E1-ND.

The affinity analysis was performed with immobilized biotinylated peptides, i.e., E1-RE (alt), E1-SE (alt), E1-KE (alt), E1-NE (alt) and E1-ND. Some of the tested clones were able to recognize all five variants. Examples of clones recognizing 1, 2, 3, 4 or 5 sequence variants are listed in Table 2.

TABLE 2

| Clone name | Recognized peptide variants | | | | | Whole Tat protein |
|---|---|---|---|---|---|---|
| A | — | — | E1-SE (alt) | — | — | — |
| B | E1-RE (alt) | E1-KE (alt) | — | — | — | Tat |
| C | E1-RE (alt) | E1-KE (alt) | E1-SE (alt) | — | — | Tat |
| D | E1-RE (alt) | E1-KE (alt) | E1-SE (alt) | E1-NE (alt) | — | Tat |
| pan-Epitope 1 #5 | E1-RE (alt) | E1-KE (alt) | E1-SE (alt) | E1-NE (alt) | E1-ND | Tat |

Based on these ELISA results, 8 clones that bound immobilised Epitope 1-containing Tat protein/peptide and free Tat protein, were found. These clones were large scale expressed and purified on Ni-NTA sepharose for further analysis in a Biacore assay (For data calculation BIA evaluation 3.2 and model 1:1 Langmuir binding was used; See Biacore manual).

Two clones (referred to as pan-epitope 1 #5 and pan-epitope 1 #6) out of eight clones bound to all five Epitope 1 peptides with high affinity. See Table 3.

TABLE 3

Affinity analysis of anti-Tat scFv against immobilized peptides

| ScFv | Pep | | | | |
|---|---|---|---|---|---|
| | E1-RE (alt) $k_a$ $k_d$ $K_D$ | E1-KE (alt) $k_a$ $k_d$ $K_D$ | E1-SE (alt) $k_a$ $k_d$ $K_D$ | E1-NE (alt) $k_a$ $k_d$ $K_D$ | E1-ND $k_a$ $k_d$ $K_D$ |
| pan-epitope 1 #5 | $5 \times 10^5$ $2 \times 10^{-3}$ $3 \times 10^{-9}$ | $4 \times 10^5$ $2 \times 10^{-3}$ $5 \times 10^{-9}$ | $4 \times 10^5$ $2 \times 10^{-3}$ $5 \times 10^{-9}$ | $6 \times 10^5$ $4 \times 10^{-3}$ $6 \times 10^{-9}$ | $4 \times 10^5$ $8 \times 10^{-3}$ $2 \times 10^{-8}$ |
| pan-epitope 1 #6 | $5 \times 10^5$ $3 \times 10^{-3}$ $5 \times 10^{-9}$ | $5 \times 10^5$ $4 \times 10^{-3}$ $7 \times 10^{-9}$ | $6 \times 10^5$ $4 \times 10^{-3}$ $7 \times 10^{-9}$ | $1 \times 10^6$ $1 \times 10^{-2}$ $9 \times 10^{-9}$ | $1 \times 10^6$ $3 \times 10^{-2}$ $2 \times 10^{-8}$ |

D. Conversion to Full $IgG_1$ Antibody

The clones pan-epitope 1 #5 and pan-epitope 1 #6 were converted into full $IgG_1$ antibodies. The VH and VL genes from scFv pan-epitope 1 #5 and pan-epitope 1 #6 were PCR amplified. The PCR fragments produced were restriction enzyme digested and ligated into proprietary expression vectors modified from pcDNA3. The expression vectors contain γ1 genomic constant region (NCBI database accession number Z17370) for insertion of PCR amplified VH genes or the λ genomic constant region (NCBI database accession number X06875) for insertion of PCR amplified VL genes.

The resulting heavy and light chain constructs were then produced in large scale using NucleoBond Plasmid Mega Kit (BD Biosciences, cat. No K3004-1). The plasmid DNA was spin purified employing MicroSpin S-400 HR columns (Amersham Biosciences, cat. No 27-5240-01) and used to transiently transfect COS-7 green monkey cells (ATCC Accession No. CRL-1651).

COS-7 cells were cultivated at 37° C., 5% $CO_2$ in D-MEM (Invitrogen, cat. No. 31966-021) and supplemented with 10% Fetal Bovine Serum (Invitrogen, cat. No. 26140-079) and 1x non-essential amino acids (Invitrogen, cat. No. 11140-035). Transfections were performed using Lipofectamine 2000 (Invitrogen, cat. No. 11668-019) in accordance with the manufacturer's protocol. 20 hours post transfection, the cell culture media was replaced with D-MEM medium (Invitrogen, cat. No. 31966-021) and supplemented with 10% Ultra-Low IgG Fetal Bovine Serum (Invitrogen, cat. No. 16250-078) and 1x non essential amino acids (Invitrogen, cat. No 11140-035).

After a five days incubation period the cell culture media was harvested and the full IgG molecules retrieved.

E. Screening of IgG

Converted IgG1 molecules transiently expressed in COS-7 cells were purified on a protein A column. Purified material was further characterized by SDS-PAGE, gel filtration chromatography, isolectric focusing, dose response ELISA and LAL-test. Only one $IgG_1$ pan-Epitope 1 antibody expressed in acceptable levels in initial tests. The second $IgG_1$ pan-Epitope 1 antibdy #6 has not been further analysed. The $IgG_1$ pan-epitope 1 antibody variable region H1 was sequenced and found to be FSDYYMSWIRQAPG (SEQ ID NO: 41).

Affinity determination between $IgG_1$ pan-epitope 1 antibody #5 and the Epitope 1 peptides or whole Tat protein was performed with a Biacore assay. Eight specific biotinylated peptides plus a control peptide were immobilised to streptavidin chips (Biacore SA-chip, BR-1000-32). Because the peptides are immobilised and the IgGs are bivalent, the apparent kinetic constants reported in the Tables 5A-5B and 6 below may partly be the result of avidity. No background binding to the chip matrix or to unrelated peptides was detected, see Tables 5A-5B and 6. Recombinant Tat protein expressed by ATG, USA containing aa 1-86 was used. Its sequence is identical to that listed in Table 1 with one exception, i.e., the amino acid at residue 42, an alanine, was replaced by a glycine.

TABLE 4A

Affinity between immobilised biotinylated-peptides and $IgG_1$ pan-epitope 1 antibody #5

| IgG1 | Pep | | | |
|---|---|---|---|---|
| | E1-RE (alt) $k_a$ $k_d$ $K_D$ | E1-KE (alt) $k_a$ $k_d$ $K_D$ | E1-NE (alt) $k_a$ $k_d$ $K_D$ | E1-SE (alt) $k_a$ $k_d$ $K_D$ |
| $IgG_1$ pan-epitope 1 antibody #5 | $9.5 \times 10^5$ $9.0 \times 10^{-6}$ $9.5 \times 10^{-12}$ | $1.3 \times 10^6$ $1.3 \times 10^{-5}$ $1.0 \times 10^{-11}$ | $1.2 \times 10^6$ $1.6 \times 10^{-5}$ $1.4 \times 10^{-11}$ | $1.0 \times 10^6$ $1.4 \times 10^{-5}$ $1.4 \times 10^{-11}$ |

TABLE 4B

| IgG1 | Pep | | | |
|---|---|---|---|---|
| | E1-RD (alt) $k_a$ $k_d$ $K_D$ | E1-KD (alt) $k_a$ $k_d$ $K_D$ | E1-ND $k_a$ $k_d$ $K_D$ | E1-SD (alt) $k_a$ $k_d$ $K_D$ |
| $IgG_1$ pan-epitope 1 antibody #5 | $3.4 \times 10^6$ $4.2 \times 10^{-5}$ $1.2 \times 10^{-11}$ | $1.0 \times 10^7$ $9.4 \times 10^{-5}$ $9.0 \times 10^{-12}$ | $7.4 \times 10^5$ $3.2 \times 10^{-5}$ $4.3 \times 10^{-11}$ | $1.5 \times 10^7$ $1.0 \times 10^{-4}$ $6.9 \times 10^{-12}$ |

TABLE 5

Affinity between amino-coupled α-Tat $IgG_1$ and Tat protein

| IgG1 | Aff. constant | | |
|---|---|---|---|
| | $k_a$ | $k_d$ | $K_D$ |
| $IgG_1$ pan-epitope 1 antibody #5 | $7 \times 10^3$ | $3 \times 10^{-5}$ | $4 \times 10^{-9}$ |

Example 2

Functional In Vitro Studies

The ability of $IgG_1$ pan-epitope 1 antibody #5 to inhibit HIV-1 replication was tested in a set of experiments performed at Karolinska Institutet, Stockholm, Sweden. The experiments were based on HIV-1 strain IIIB infected Jurkat cells in which viral replication was monitored through an ELISA directed against the HIV-1 gag protein p 24 (Re, et al., 1995 J. Acq. Imm. Def. Syndromes and Human Retrovir., 10, 408-416).

In the virus infection procedure, exponentially growing Jurkat cells were infected with virus inoculum for 1 hour at +37° C., whereupon the cells were washed and re-suspended in medium (RPMI-1640 medium with Glutamax reagent, 10% FCS, 50 IU/ml Penicillin and 50 μg/ml Streptomycin). Infected cells were mixed with uninfected cells in various concentrations. At the same time anti-Tat $IgG_1$ or control anti-FITC (Söderlind et al., 2000 Nat. Biotech., 18 (8): 852-856) was added to the culture in increasing concentrations. The cultures were incubated at +37° C. in 5% $CO_2$.

After 3-4 days the cultures were split and re-fed with fresh medium plus antibodies. Virus levels were determined through a p24 detecting ELISA at day 7 post infection.

Figure 2:
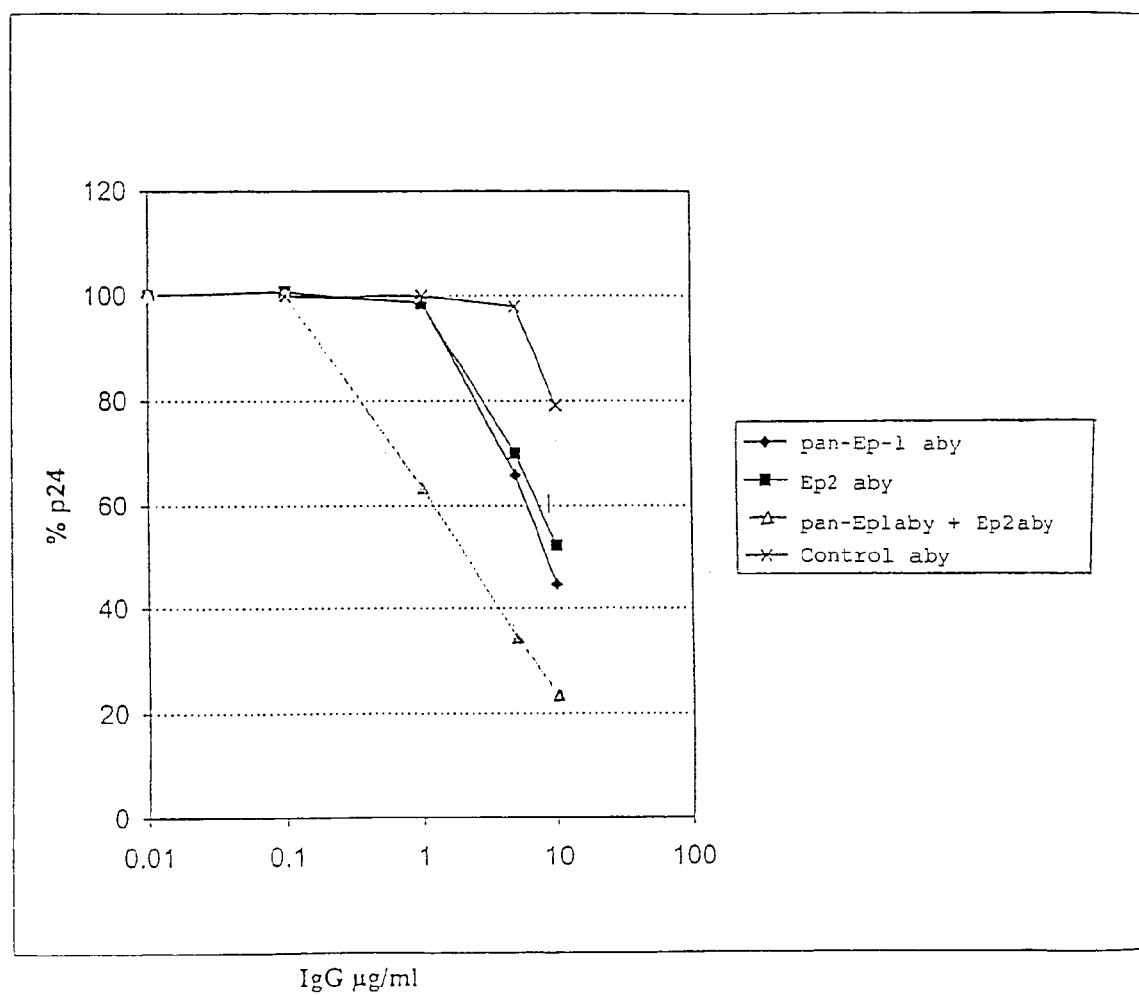
FIG. 2 is a graph plotting inhibition in the assay of FIG. 1 for the same pan-Epitope 1 IgG antibody (pan-Ep-1; diamond), for a monoclonal antibody that binds Epitope 2 (Ep 2 aby; square), for both monoclonal antibodies used together (triangle) and for use of the antibody control (X) at a dosage of 10 TCID50. The resulting curve (triangle) indicates a synergy in the operation of the assay when using both a pan-Epitope 1 antibody and an Epitope 2 antibody compared to the results generated by either pan-Epitope 1 antibody (diamond) or Epitope 2 antibody (square) alone.

FIGS. 1 and 2 provide the supporting data from this assay. FIG. 1 shows the experiment performed with 1% initially infected cells. The $IC_{50}$ value for $IgG_1$ pan-epitope 1 antibody #5, calculated from inhibition experiments performed with 1% and 3% initially infected cells, was 0.14 μg/ml and 0.44 μg/ml, respectively. Thus FIG. 1 demonstrates dose-related inhibition of HIV-1 replication by a pan-Epitope 1 antibody of this invention. FIG. 2 demonstrates that a pan-Epitope 1 antibody and an antibody to Tat Epitope 2, used singly, have similar dose-related inhibition curves. When the two antibodies are used in combination, a synergistic response is generated. The combination of the two antibodies surprisingly produces a 10-fold more potent inhibition in viral levels than is produced by either antibody used alone. This indicates an unexpected, but additional valuable therapeutic composition and method for inhibition of HIV-1 viral levels by using a pan-Epitope 1 antibody in concert with an anti-Epitope 2 antibody.

Example 3

Assay for Measuring Levels of Tat

According to a competition assay format, a single pan-Epitope 1 antibody, preferably a pan-Epitope 1 antibody, which is labelled with a detectable label, is employed. Before performing the assay, a plate is coated with HIV-1 Tat protein. A suboptimal or subsaturation dilution of the pan-Epitope 1 antibody and a plasma sample containing a known amount of HIV-1 Tat are added to the plate. A standard binding curve is measured for binding of the pan-Epitope 1 antibody to the Tat on the plate. The more HIV-1 Tat in the plasma sample, the less binding of the pan-Epitope 1 antibody.

Figure 3:
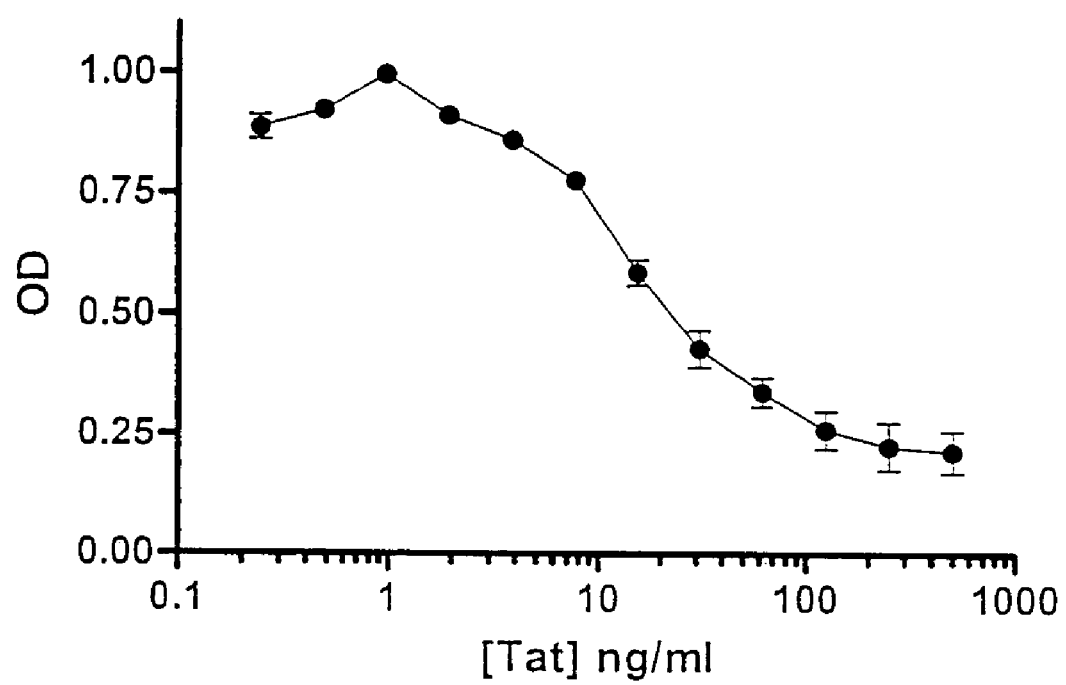
FIG. 3 is a graph showing the results of a competition assay, in which 200 ng/ml Tat are coated on a plate. Samples containing increasing amounts of HIV-1 Tat in buffer compete with the coated Tat for binding by 10 ng of a detector pan-Epitope 1 antibody, labelled with biotin. As the amount of Tat in the samples increases, the amounts of binding of the pan-Epitope 1 antibody to the plate decreases. Binding is detected by use of a goat anti-human antibody IgG-horse radish peroxidase (HRP) reagent, in which the reagent binds to the biotin on the bound pan-Epitope 1 antibody. The antibody is the same as that used in FIG. 1.

FIG. 3 illustrates the results of such an assay. A plate coated with 200 ng/ml Tat was contacted with patient buffer samples containing increasing amounts of HIV-1 Tat and a suboptimal 10 ng of a pan-Epitope 1 antibody, labelled with biotin. Competition for the binding of the pan-Epitope 1 antibody occurred between the bound HIV-1 Tat sequences on the coated plate and HIV-1 Tat sequences in the sample.

As the amount of Tat in the sample increased, the amount of binding of the pan-Epitope 1 antibody to the plate decreased.

Binding was detected by addition of an anti-human IgG bound to streptavidin. The IgG bound to the pan-Epitope 1 antibody. After the plate was washed, horse radish peroxidase was added to the plate and a detectable signal proportional to the amount of bound pan-Epitope 1 antibody was produced. By measuring the amount of pan Epitope 1 antibody bound to the plate in the sample and comparing it to the standard binding curve, the amount of HIV-1 Tat in the sample was calculated. It is clear to one of skill in the art, as detailed above, that other signal generating labels may be employed in this assay and that the selection of the signal generating system is not a limitation on this assay.

Figure 4:
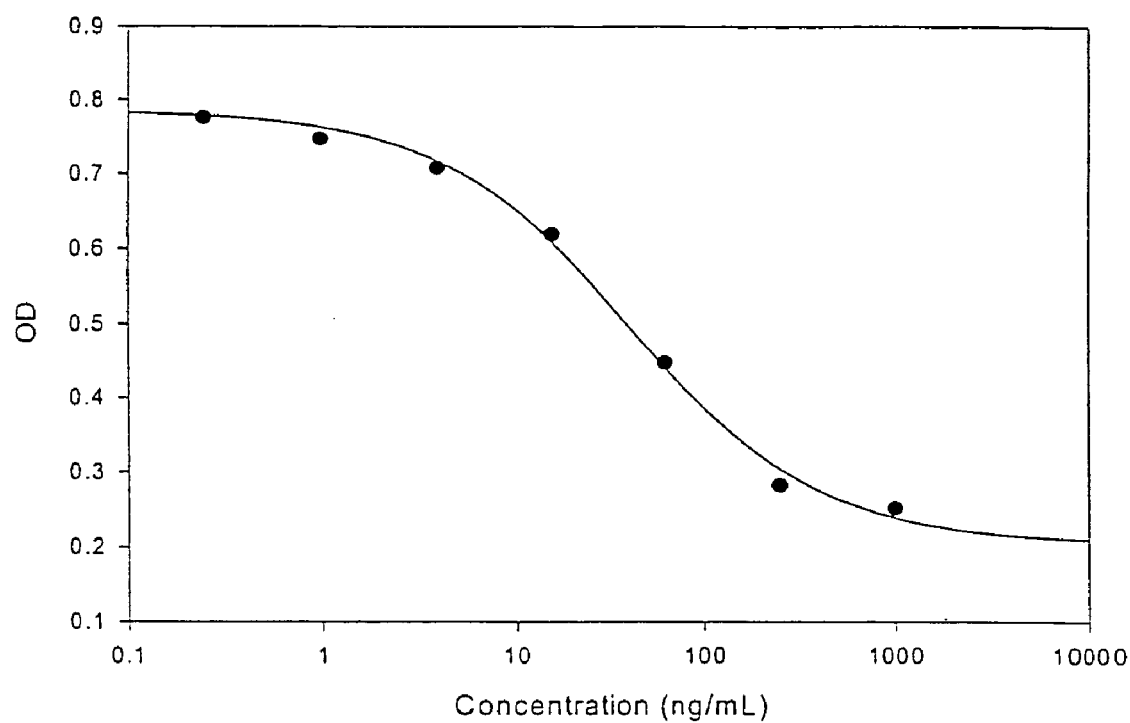
FIG. 4 is a recombinant Tat dose response curve in human plasma generated by a competitive assay, similar to that described in FIG. 3, run in 50% plasma. A typical dose-response curve is generated, indicating that no interference was generated by plasma to the binding of the pan-Epitope 1 antibody to Tat in the sample. The antibody is the same as that used in FIG. 1.

FIG. 4 is a recombinant Tat dose response curve in human plasma generated by a competitive assay, similar to that described above and run in 50% plasma. A typical dose-response curve was generated, indicating that no interference was generated by plasma to the binding of the pan-Epitope 1 antibody to Tat in the sample. This assay permitted measurement of patient plasma Tat levels.

Figure 5:
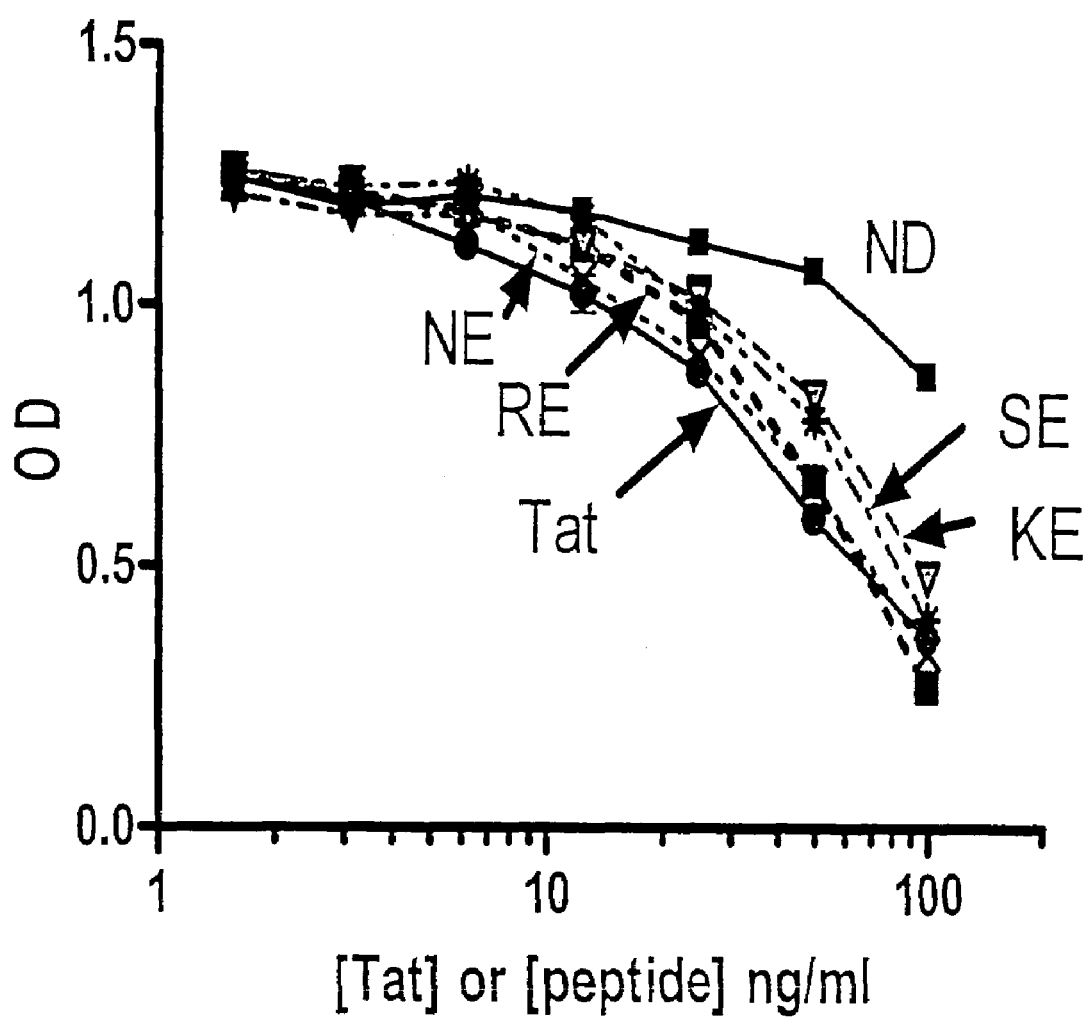
FIG. 5 is a graph showing comparative dose response curves for the recombinant Tat (rTat) and peptides corresponding to Tat Epitope 1 variants in buffer in an assay similar to that of FIG. 3. Tat (200 ng/ml) is coated on a plate. The peptides are labeled as E1-RE ("RE"), E1-NE ("NE"), E1-SE ("SE"), E1-KE ("KE"), E1-ND ("ND") and full length Tat ("Tat"). These peptides and alternative variants, designated as "alt", are defined in Table 1 below. Concentrations of the pan-Epitope-1 antibody were 10 ng/ml. All resulting binding curves are similar indicating that all variants provide similar results Note that as used throughout this specification, both the shorter biotinylated peptides and the longer ("alt") biotinylated peptides yield the same results.

Similar assays in buffer were run to produce comparative dose response curves for the recombinant Tat and Epitope 1 variant peptides and the results are demonstrated in the graph of FIG. 5. The peptides tested were E1-RE, E1-NE, E1-SE, E1-KE, E1-ND and full length Tat. All curves are similar indicating that all variants provide similar results.

Figure 6A:
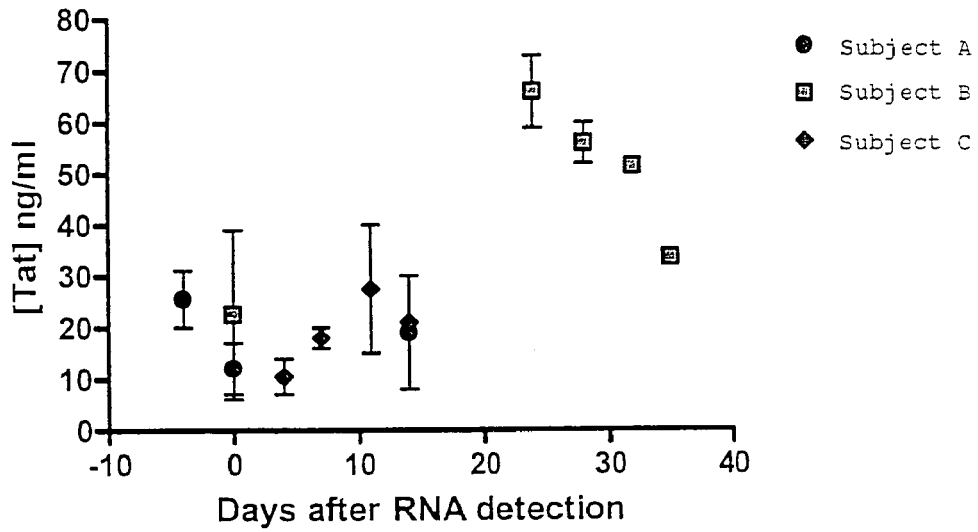
FIG. 6A is a graph generated by a competitive assay similar to that of FIG. 3 in three HIV-1 infected human subjects. The subjects are identified by number and symbol, i.e., Subject A (circle), Subject B (square) and Subject C (diamond). The competitive assay of this invention using the pan-Epitope 1 antibody of FIG. 1 is shown to be useful in identifying levels of Tat RNA (ng/ml) over days after RNA detection in infected plasma.
Figure 6B:
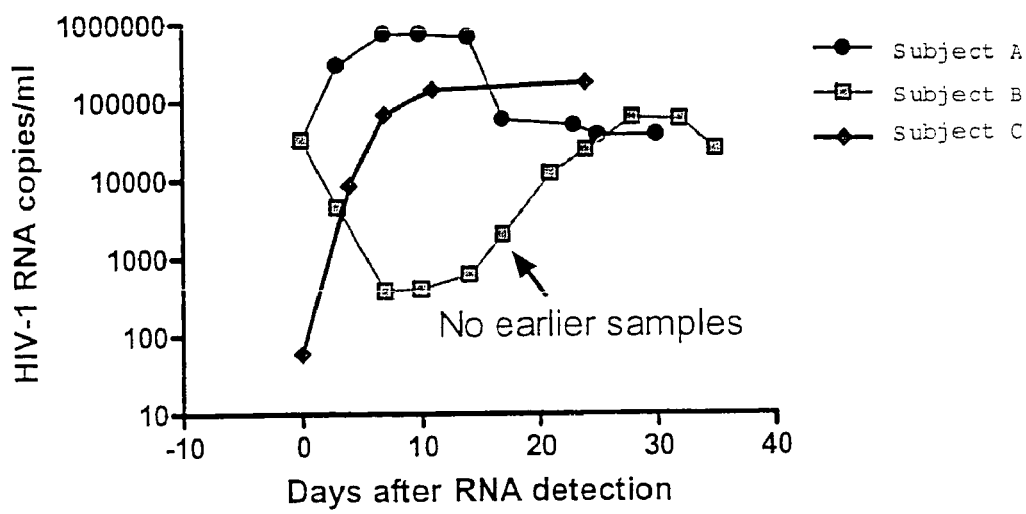
FIG. 6B is a similar graph for the patients of FIG. 6A, measuring virus titer (RNA copies/ml) per day after initial RNA detection. Note that Subject B had recovered from acute infection at time 0.

Finally, a set of competitive assays as described above were performed in three HIV-1 infected human subjects. As represented in FIGS. 6A and 6B, the subjects were identified by number and symbol, i.e., Subject A (circle), Subject B (square) and Subject C (diamond). The competitive assay of this invention using the pan-Epitope antibody E9 was shown to be useful in identifying levels of Tat RNA and virus titer over days after RNA detection in infected plasma. These data demonstrated that the competition assay of the present invention using a single pan Epitope 1 antibody was able to detect Tat levels in clinical samples and thus confirm HIV-1 infection by detecting Tat-encoded protein in infected subjects.

As demonstrated by the examples and data reported above, one advantage of the competition assay format is that the number of reagents (antibodies) employed in the assay are reduced. One uses the pan-Epitope 1 antibody in place of a cocktail of monoclonal antibodies directed to multiple sequences of SEQ ID NO: 5, to accomplish detection of multiple strains and subtypes of HIV-1 Tat in a single assay.

Example 4

Tat Bioassay and Inhibition by IgG1 Pan-Epitope 1 Antibody #5

Normal human peripheral blood mononuclear cells (PBMC) do not sustain HIV-1 replication, but are rendered permissive for HIV-1 replication after activation by mitogens or by HIV-1 Tat protein in vitro (Li C J et al. 1997 Proc Natl Acad Sci USA 94:8116-1820). Furthermore, Li et al. demonstrated that Tat induced permissivity could be inhibited by polyclonal or monoclonal antibodies to Tat. This approach was used to develop a bioassay for monoclonal antibody (Mab) inhibition of Tat-induced permissivity to HIV-1 replication in human PBMC.

PBMC lot # 03AP04 (Astarte Biologics) and recombinant Tat, expressed in *E coli* and purified by reverse phase chromatography (ATG, Inc.) were used for the xperiments.

100 μl of cells ($5 \times 10^6$/ml) were used per well and 100 μl of Tat alone at various concentrations, or 10 ng/ml Tat preincubated with various concentrations of monoclonal antibody, were added to the cells and incubated for 5 days at 37° C. with 5-6% $CO_2$ and 80-90% humidity. Flat bottom 96 well tissue culture plates were used.

After 5 days media was pipetted in the wells to release cells from the plate surface and the cells were transferred to a V-bottom 96 well plate and washed thoroughly. 100 μl of a 1/10 dilution of purified HIV-1 viral lysate (BIII) (Zeptometrix Corp.) was added to each well and incubated for 4 hours. This represented 35 ng units of HIV-1 protein p24 per well.

After 4 hours the cells were thoroughly washed, resuspended in tissue culture medium, and incubated for 4-5 additional days. At termination the cells were spun at 400×g for 10 minutes and the supernatants were harvested. The supernatants were assayed for HIV-1 p24 using Zeptometrix RET-ROtek™ HIV-1 p24 Antigen ELISA, as per the manufacturer's recommendations.

Ten (10) replicate wells were used for the control containing no Tat (0 Tat); 10 replicate wells were used containing 10 ng/ml Tat. All other wells had 5 replicates. The data were entered into a Prism GraphPad™ program and analyzed statistically by one way ANOVA followed by analysis of between column differences with correction for multiple analyses.

Figure 7:
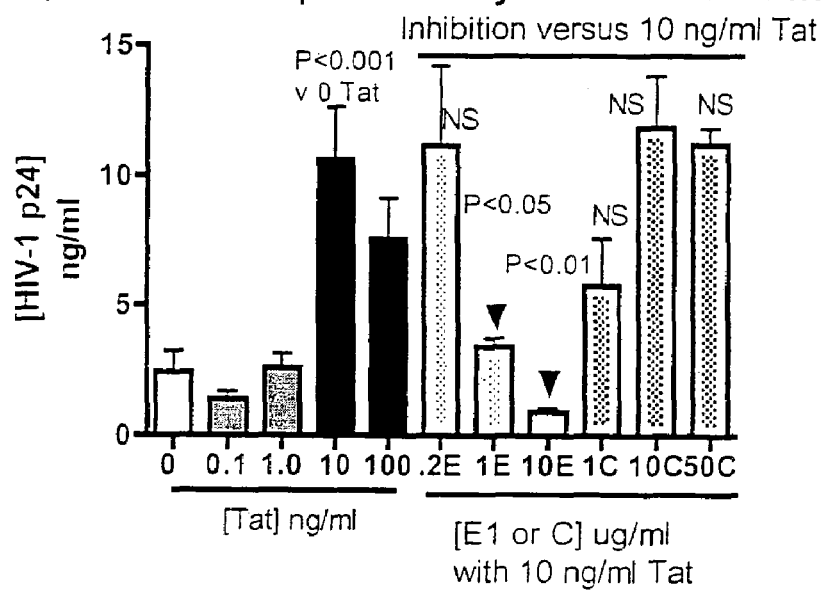
FIG. 7 is a graph showing HIV-1 replication as a function of Tat activation and of inhibition by the IgG1 pan epitope #5 antibody, i.e., an antibody that binds five Epitope 1 variants, in normal human peripheral blood mononuclear cells (PM-BCs). The first five columns reflect varying levels, i.e., 0, 0.1, 1.0, 10, and 100 ng/ml concentrations of Tat. The optimal concentration for induction of HIV-1 replication was determined to be 10 ng/ml, as shown in the figure. The last six columns show inhibition of HIV-1 replication at varying concentrations of IgG1 pan-epitope # 5 antibody in PBMCs exposed to the optimal 10 ng/ml concentration of Tat. As indicated in the figure, pan-epitope # 5 antibody is represented by arbitrary reference character "E", and results for antibody concentrations of 0.2 μg/ml, 1 μg/ml, and 10 μg/ml are shown along with control IgG1 antibody at 1, 10, and 50 μg/ml concentrations. Note that inhibition of HIV-1 replication was not significant (NS) in all controls (represented by the arbitrary reference character "C") as well as in the 0.2 µg/ml concentration of IgG1 pan-epitope # 5 antibody, i.e., p>0.05.

The results are presented in FIG. 7 and show that 10 ng/ml renders PBMC permissive for HIV-1 replication ($P<0.001$). This permissivity is inhibited by 1 μg/ml ($P<0.05$) and 10 μg/ml ($P<0.01$) IgG1 pan-epitope 1 #5 antibody, but not by the control IgG1 antibody at 1, 10 or 50 μg/ml.

Thus, the presence of a pan-Epitope 1 antibody, i.e., a single antibody that binds to five Epitope 1 variants, demonstrated the ability to inhibit HIV-1 replication by inhibiting Tat in human PBMC.

Numerous modifications and variations of the present invention are included in this specification and are expected to be obvious to one of skill in the art. Such modifications and alterations to the compositions and processes of the present invention are believed to be encompassed in the scope of the claims appended hereto. All documents listed or referred to above are incorporated herein by reference.

The invention claimed is:

1. A single isolated antibody or antibody fragment which binds five variant sequences, wherein each variant sequence is represented by the formula $R_1$-Asp-Pro-$X_7$-Leu-$Y_9$-Pro-$R_2$ (SEQ ID NO: 5), wherein $X_7$ is Arg, Lys, Ser or Asn;
wherein $Y_9$ is Glu or Asp;
wherein $R_1$ is Val;
wherein $R_2$ is absent; and
wherein said single isolated antibody or antibody fragment binds to HIV-1 Tat protein from at least five HIV-1 strains and subtypes.

2. The single isolated antibody or antibody fragment of claim 1, wherein said variant sequences are selected from the group consisting of
   (a) SEQ ID NO: 5, wherein $R_1$ is Val, $R_2$ is absent, $X_7$ is Arg and $Y_9$ is Glu;
   (b) SEQ ID NO: 5, wherein $R_1$ is Val, $R_2$ is absent, $X_7$ is Lys and $Y_9$ is Glu;
   (c) SEQ ID NO: 5, wherein $R_1$ is Val, $R_2$ is absent, $X_7$ is Ser and $Y_9$ is Glu;
   (d) SEQ ID NO: 5, wherein $R_1$ is Val, $R_2$ is absent, $X_7$ is Asn and $Y_9$ is Glu;
   (e) SEQ ID NO: 5, wherein $R_1$ is Val, $R_2$ is absent, $X_7$ is Arg and $Y_9$ is Asp;
   (f) SEQ ID NO: 5, wherein $R_1$ is Val, $R_2$ is absent, $X_7$ is Lys and $Y_9$ is Asp;
   (g) SEQ ID NO: 5, wherein $R_1$ is Val, $R_2$ is absent, $X_7$ is Ser and $Y_9$ is Asp; and
   (h) SEQ ID NO: 5, wherein $R_1$ is Val, $R_2$ is absent, $X_7$ is Asn and $Y_9$ is Asp.

3. The single isolated antibody or antibody fragment according to claim 2, which binds at least one of said variant sequences selected from the group consisting of (a) through (d) and at least one of said variant sequences selected from the group consisting of (e) through (h).

4. The single isolated antibody or antibody fragment according to claim 2, which binds to the five variant sequences (a), (b), (c), (d) and (h).

5. The single isolated antibody or antibody fragment according to claim 1, which is selected from the group consisting of a monoclonal antibody, a synthetic antibody, a recombinant antibody, a chimeric antibody, a humanized antibody, a human antibody, an isolated single antibody chain, and a fragment of said antibodies or antibody chain.

6. A composition comprising an antibody or antibody fragment of claim 1 and a pharmaceutically acceptable carrier.

7. A single isolated antibody or antibody fragment which binds the five sequences represented by the formula $R_1$-Asp-Pro-$X_7$-Leu-$Y_9$-Pro-$R_2$ (SEQ ID NO: 5), wherein $X_7$ is Arg, Lys, Ser or Asn;
wherein $Y_9$ is Glu or Asp;
wherein $R_1$ is Val;
wherein $R_2$ is absent; and
wherein one sequence is Val-Asp-Pro-Arg-Leu-Glu-Pro, wherein one sequence is Val-Asp-Pro-Lys-Leu-Glu-Pro,
wherein one sequence is Val-Asp-Pro-Ser-Leu-Glu-Pro,
wherein one sequence is Val-Asp-Pro-Asn-Leu-Glu-Pro, and
wherein one sequence is Val-Asp-Pro-Asn-Leu-Asp-Pro.

8. The single isolated antibody or antibody fragment according to claim 7, which is selected from the group consisting of a monoclonal antibody, a synthetic antibody, a recombinant antibody, a chimeric antibody, a humanized antibody, a human antibody, an isolated single antibody chain, and a fragment of said antibodies or antibody chain.

9. A composition comprising an antibody or antibody fragment of claim 7, and a pharmaceutically acceptable carrier.

* * * * *

SEQUENCE LISTING

<160> NUMBER OF SEQ ID NOS: 41

<210> SEQ ID NO 1
<211> LENGTH: 9
<212> TYPE: PRT
<213> ORGANISM: Human immunodeficiency virus type 1
<220> FEATURE:
<221> NAME/KEY: MISC_FEATURE
<222> LOCATION: (4)..(4)

```
<223> OTHER INFORMATION: Xaa can be Arg, Lys, Ser or Asn
<220> FEATURE:
<221> NAME/KEY: MISC_FEATURE
<222> LOCATION: (6)..(6)
<223> OTHER INFORMATION: Xaa can be Glu or Asp
<220> FEATURE:
<221> NAME/KEY: MISC_FEATURE
<222> LOCATION: (9)..(9)
<223> OTHER INFORMATION: Xaa can be Lys or Asn

<400> SEQUENCE: 1

Val Asp Pro Xaa Leu Xaa Pro Trp Xaa
1               5

<210> SEQ ID NO 2
<211> LENGTH: 11
<212> TYPE: PRT
<213> ORGANISM: Human immunodeficiency virus type 1
<220> FEATURE:
<221> NAME/KEY: MISC_FEATURE
<222> LOCATION: (2)..(2)
<223> OTHER INFORMATION: Xaa can be Gly or Ala

<400> SEQUENCE: 2

Lys Xaa Leu Gly Ile Ser Tyr Gly Arg Lys Lys
1               5                   10

<210> SEQ ID NO 3
<211> LENGTH: 7
<212> TYPE: PRT
<213> ORGANISM: Human immunodeficiency virus type 1
<220> FEATURE:
<221> NAME/KEY: MISC_FEATURE
<222> LOCATION: (3)..(3)
<223> OTHER INFORMATION: Xaa can be Ala, Pro, Ser or Gln
<220> FEATURE:
<221> NAME/KEY: MISC_FEATURE
<222> LOCATION: (4)..(4)
<223> OTHER INFORMATION: Xaa can be Pro or His
<220> FEATURE:
<221> NAME/KEY: MISC_FEATURE
<222> LOCATION: (5)..(5)
<223> OTHER INFORMATION: Xaa can be Gln or Pro
<220> FEATURE:
<221> NAME/KEY: MISC_FEATURE
<222> LOCATION: (6)..(6)
<223> OTHER INFORMATION: Xaa can be Asp, Asn, Gly or Ser

<400> SEQUENCE: 3

Arg Arg Xaa Xaa Xaa Xaa Ser
1               5

<210> SEQ ID NO 4
<211> LENGTH: 12
<212> TYPE: PRT
<213> ORGANISM: Human immunodeficiency virus type 1
<220> FEATURE:
<221> NAME/KEY: MISC_FEATURE
<222> LOCATION: (3)..(3)
<223> OTHER INFORMATION: Xaa can be Asn or Thr
<220> FEATURE:
<221> NAME/KEY: MISC_FEATURE
<222> LOCATION: (6)..(6)
<223> OTHER INFORMATION: Xaa can be Ala or Val

<400> SEQUENCE: 4

Ser Gln Xaa His Gln Xaa Ser Leu Ser Lys Gln Pro
1               5                   10

<210> SEQ ID NO 5
<211> LENGTH: 15
```

```
<212> TYPE: PRT
<213> ORGANISM: Human immunodeficiency virus type 1
<220> FEATURE:
<221> NAME/KEY: MISC_FEATURE
<222> LOCATION: (1)..(1)
<223> OTHER INFORMATION: Xaa can be absent or Val or Glu
<220> FEATURE:
<221> NAME/KEY: MISC_FEATURE
<222> LOCATION: (2)..(2)
<223> OTHER INFORMATION: Xaa can be absent or Val or Pro
<220> FEATURE:
<221> NAME/KEY: MISC_FEATURE
<222> LOCATION: (3)..(3)
<223> OTHER INFORMATION: Xaa can be absent or Val
<220> FEATURE:
<221> NAME/KEY: MISC_FEATURE
<222> LOCATION: (6)..(6)
<223> OTHER INFORMATION: Xaa can be Arg or Lys or Ser or Asn
<220> FEATURE:
<221> NAME/KEY: MISC_FEATURE
<222> LOCATION: (8)..(8)
<223> OTHER INFORMATION: Xaa can be Glu or Asp
<220> FEATURE:
<221> NAME/KEY: MISC_FEATURE
<222> LOCATION: (10)..(10)
<223> OTHER INFORMATION: Xaa can be absent or Trp
<220> FEATURE:
<221> NAME/KEY: MISC_FEATURE
<222> LOCATION: (11)..(11)
<223> OTHER INFORMATION: Xaa can be absent or Lys or Asn
<220> FEATURE:
<221> NAME/KEY: MISC_FEATURE
<222> LOCATION: (12)..(12)
<223> OTHER INFORMATION: Xaa can be absent or His
<220> FEATURE:
<221> NAME/KEY: MISC_FEATURE
<222> LOCATION: (13)..(13)
<223> OTHER INFORMATION: Xaa can be absent or Pro
<220> FEATURE:
<221> NAME/KEY: MISC_FEATURE
<222> LOCATION: (14)..(14)
<223> OTHER INFORMATION: Xaa can be absent or Gly
<220> FEATURE:
<221> NAME/KEY: MISC_FEATURE
<222> LOCATION: (15)..(15)
<223> OTHER INFORMATION: Xaa can be absent or Ser

<400> SEQUENCE: 5

Xaa Xaa Xaa Asp Pro Xaa Leu Xaa Pro Xaa Xaa Xaa Xaa Xaa Xaa
1               5                   10                  15

<210> SEQ ID NO 6
<211> LENGTH: 13
<212> TYPE: PRT
<213> ORGANISM: Human immunodeficiency virus type 1
<220> FEATURE:
<221> NAME/KEY: MISC_FEATURE
<222> LOCATION: (9)..(9)
<223> OTHER INFORMATION: Xaa can be Lys or Asn
<220> FEATURE:
<221> NAME/KEY: MISC_FEATURE
<222> LOCATION: (10)..(10)
<223> OTHER INFORMATION: Xaa can be absent or His
<220> FEATURE:
<221> NAME/KEY: MISC_FEATURE
<222> LOCATION: (11)..(11)
<223> OTHER INFORMATION: Xaa can be absent or Pro
<220> FEATURE:
<221> NAME/KEY: MISC_FEATURE
<222> LOCATION: (12)..(12)
<223> OTHER INFORMATION: Xaa can be absent or Gly
<220> FEATURE:
<221> NAME/KEY: MISC_FEATURE
<222> LOCATION: (13)..(13)
<223> OTHER INFORMATION: Xaa can be absent or Ser

<400> SEQUENCE: 6
```

Val Asp Pro Arg Leu Glu Pro Trp Xaa Xaa Xaa Xaa Xaa
1               5                   10

<210> SEQ ID NO 7
<211> LENGTH: 13
<212> TYPE: PRT
<213> ORGANISM: Human immunodeficiency virus type 1
<220> FEATURE:
<221> NAME/KEY: MISC_FEATURE
<222> LOCATION: (9)..(9)
<223> OTHER INFORMATION: Xaa can be Lys or Asn
<220> FEATURE:
<221> NAME/KEY: MISC_FEATURE
<222> LOCATION: (10)..(10)
<223> OTHER INFORMATION: Xaa can be absent or His
<220> FEATURE:
<221> NAME/KEY: MISC_FEATURE
<222> LOCATION: (11)..(11)
<223> OTHER INFORMATION: Xaa can be absent or Pro
<220> FEATURE:
<221> NAME/KEY: MISC_FEATURE
<222> LOCATION: (12)..(12)
<223> OTHER INFORMATION: Xaa can be absent or Gly
<220> FEATURE:
<221> NAME/KEY: MISC_FEATURE
<222> LOCATION: (13)..(13)
<223> OTHER INFORMATION: Xaa can be absent or Ser

<400> SEQUENCE: 7

Val Asp Pro Lys Leu Glu Pro Trp Xaa Xaa Xaa Xaa Xaa
1               5                   10

<210> SEQ ID NO 8
<211> LENGTH: 13
<212> TYPE: PRT
<213> ORGANISM: Human immunodeficiency virus type 1
<220> FEATURE:
<221> NAME/KEY: MISC_FEATURE
<222> LOCATION: (9)..(9)
<223> OTHER INFORMATION: Xaa can be Lys or Asn
<220> FEATURE:
<221> NAME/KEY: MISC_FEATURE
<222> LOCATION: (10)..(10)
<223> OTHER INFORMATION: Xaa can be absent or His
<220> FEATURE:
<221> NAME/KEY: MISC_FEATURE
<222> LOCATION: (11)..(11)
<223> OTHER INFORMATION: Xaa can be absent or Pro
<220> FEATURE:
<221> NAME/KEY: MISC_FEATURE
<222> LOCATION: (12)..(12)
<223> OTHER INFORMATION: Xaa can be absent or Gly
<220> FEATURE:
<221> NAME/KEY: MISC_FEATURE
<222> LOCATION: (13)..(13)
<223> OTHER INFORMATION: Xaa can be absent or Ser

<400> SEQUENCE: 8

Val Asp Pro Ser Leu Glu Pro Trp Xaa Xaa Xaa Xaa Xaa
1               5                   10

<210> SEQ ID NO 9
<211> LENGTH: 13
<212> TYPE: PRT
<213> ORGANISM: Human immunodeficiency virus type 1
<220> FEATURE:
<221> NAME/KEY: MISC_FEATURE
<222> LOCATION: (9)..(9)
<223> OTHER INFORMATION: Xaa can be Lys or Asn
<220> FEATURE:
<221> NAME/KEY: MISC_FEATURE
<222> LOCATION: (10)..(10)
<223> OTHER INFORMATION: Xaa can be absent or His -continued

```
<220> FEATURE:
<221> NAME/KEY: MISC_FEATURE
<222> LOCATION: (11)..(11)
<223> OTHER INFORMATION: Xaa can be absent or Pro
<220> FEATURE:
<221> NAME/KEY: MISC_FEATURE
<222> LOCATION: (12)..(12)
<223> OTHER INFORMATION: Xaa can be absent or Gly
<220> FEATURE:
<221> NAME/KEY: MISC_FEATURE
<222> LOCATION: (13)..(13)
<223> OTHER INFORMATION: Xaa can be absent or Ser

<400> SEQUENCE: 9

Val Asp Pro Asn Leu Glu Pro Trp Xaa Xaa Xaa Xaa Xaa
1               5                   10

<210> SEQ ID NO 10
<211> LENGTH: 13
<212> TYPE: PRT
<213> ORGANISM: Human immunodeficiency virus type 1
<220> FEATURE:
<221> NAME/KEY: MISC_FEATURE
<222> LOCATION: (9)..(9)
<223> OTHER INFORMATION: Xaa can be Lys or Asn
<220> FEATURE:
<221> NAME/KEY: MISC_FEATURE
<222> LOCATION: (10)..(10)
<223> OTHER INFORMATION: Xaa can be absent or His
<220> FEATURE:
<221> NAME/KEY: MISC_FEATURE
<222> LOCATION: (11)..(11)
<223> OTHER INFORMATION: Xaa can be absent or Pro
<220> FEATURE:
<221> NAME/KEY: MISC_FEATURE
<222> LOCATION: (12)..(12)
<223> OTHER INFORMATION: Xaa can be absent or Gly
<220> FEATURE:
<221> NAME/KEY: MISC_FEATURE
<222> LOCATION: (13)..(13)
<223> OTHER INFORMATION: Xaa can be absent or Ser

<400> SEQUENCE: 10

Val Asp Pro Asn Leu Asp Pro Trp Xaa Xaa Xaa Xaa Xaa
1               5                   10

<210> SEQ ID NO 11
<211> LENGTH: 4
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 11

Ser Gly Ser Gly
1

<210> SEQ ID NO 12
<211> LENGTH: 86
<212> TYPE: PRT
<213> ORGANISM: Human immunodeficiency virus type 1

<400> SEQUENCE: 12

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
```

-continued

```
                35                  40                  45
Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 13
<211> LENGTH: 13
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 13

Ser Gly Ser Gly Leu Gly Ile Ser Tyr Gly Arg Lys Ser
1               5                   10

<210> SEQ ID NO 14
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 14

Ser Gly Ser Gly Val Asp Pro Arg Leu Glu Pro Trp
1               5                   10

<210> SEQ ID NO 15
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 15

Ser Gly Ser Gly Val Asp Pro Lys Leu Glu Pro Trp
1               5                   10

<210> SEQ ID NO 16
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 16

Ser Gly Ser Gly Val Asp Pro Asn Leu Glu Pro Trp
1               5                   10

<210> SEQ ID NO 17
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
```

<223> OTHER INFORMATION: Biotin is attached to Ser

<400> SEQUENCE: 17

Ser Gly Ser Gly Val Asp Pro Ser Leu Glu Pro Trp
1               5                   10

<210> SEQ ID NO 18
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 18

Ser Gly Ser Gly Val Asp Pro Arg Leu Asp Pro Trp
1               5                   10

<210> SEQ ID NO 19
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 19

Ser Gly Ser Gly Val Asp Pro Lys Leu Asp Pro Trp
1               5                   10

<210> SEQ ID NO 20
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 20

Ser Gly Ser Gly Val Asp Pro Ser Leu Asp Pro Trp
1               5                   10

<210> SEQ ID NO 21
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 21

Ser Gly Ser Gly Val Asp Pro Asn Leu Asp Pro Trp
1               5                   10

<210> SEQ ID NO 22
<211> LENGTH: 15
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 22

-continued

```
Ser Gly Ser Gly Glu Pro Val Asp Pro Arg Leu Glu Pro Trp Ser
1               5                   10                  15

<210> SEQ ID NO 23
<211> LENGTH: 15
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 23

Ser Gly Ser Gly Glu Pro Val Asp Pro Lys Leu Glu Pro Trp Ser
1               5                   10                  15

<210> SEQ ID NO 24
<211> LENGTH: 15
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 24

Ser Gly Ser Gly Glu Pro Val Asp Pro Ser Leu Glu Pro Trp Ser
1               5                   10                  15

<210> SEQ ID NO 25
<211> LENGTH: 15
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 25

Ser Gly Ser Gly Glu Pro Val Asp Pro Asn Leu Glu Pro Trp Ser
1               5                   10                  15

<210> SEQ ID NO 26
<211> LENGTH: 15
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 26

Ser Gly Ser Gly Glu Pro Val Asp Pro Asn Leu Asp Pro Trp Ser
1               5                   10                  15

<210> SEQ ID NO 27
<211> LENGTH: 4
<212> TYPE: PRT
<213> ORGANISM: Human immunodeficiency virus type 1

<400> SEQUENCE: 27

His Pro Gly Ser
1

<210> SEQ ID NO 28
<211> LENGTH: 7
<212> TYPE: PRT
<213> ORGANISM: Human immunodeficiency virus type 1
```

```
<220> FEATURE:
<221> NAME/KEY: MISC_FEATURE
<222> LOCATION: (4)..(4)
<223> OTHER INFORMATION: Xaa can be Arg, Lys, Ser or Asn
<220> FEATURE:
<221> NAME/KEY: MISC_FEATURE
<222> LOCATION: (6)..(6)
<223> OTHER INFORMATION: Xaa can be Glu or Asp

<400> SEQUENCE: 28

Val Asp Pro Xaa Leu Xaa Pro
1               5

<210> SEQ ID NO 29
<211> LENGTH: 8
<212> TYPE: PRT
<213> ORGANISM: Human immunodeficiency virus type 1
<220> FEATURE:
<221> NAME/KEY: MISC_FEATURE
<222> LOCATION: (3)..(3)
<223> OTHER INFORMATION: Xaa can be Arg, Lys, Ser or Asn
<220> FEATURE:
<221> NAME/KEY: MISC_FEATURE
<222> LOCATION: (5)..(5)
<223> OTHER INFORMATION: Xaa can be Glu or Asp
<220> FEATURE:
<221> NAME/KEY: MISC_FEATURE
<222> LOCATION: (8)..(8)
<223> OTHER INFORMATION: Xaa can be Lys or Asn

<400> SEQUENCE: 29

Asp Pro Xaa Leu Xaa Pro Trp Xaa
1               5

<210> SEQ ID NO 30
<211> LENGTH: 8
<212> TYPE: PRT
<213> ORGANISM: Human immunodeficiency virus type 1
<220> FEATURE:
<221> NAME/KEY: MISC_FEATURE
<222> LOCATION: (5)..(5)
<223> OTHER INFORMATION: Xaa can be Arg, Lys, Ser or Asn
<220> FEATURE:
<221> NAME/KEY: MISC_FEATURE
<222> LOCATION: (7)..(7)
<223> OTHER INFORMATION: Xaa can be Glu or Asp

<400> SEQUENCE: 30

Glu Val Asp Pro Xaa Leu Xaa Pro
1               5

<210> SEQ ID NO 31
<211> LENGTH: 8
<212> TYPE: PRT
<213> ORGANISM: Human immunodeficiency virus type 1
<220> FEATURE:
<221> NAME/KEY: MISC_FEATURE
<222> LOCATION: (4)..(4)
<223> OTHER INFORMATION: Xaa can be Arg, Lys, Ser or Asn
<220> FEATURE:
<221> NAME/KEY: MISC_FEATURE
<222> LOCATION: (6)..(6)
<223> OTHER INFORMATION: Xaa can be Glu or Asp
<220> FEATURE:
<221> NAME/KEY: MISC_FEATURE
<222> LOCATION: (8)..(8)
<223> OTHER INFORMATION: Xaa can be Lys or Asn

<400> SEQUENCE: 31

Val Asp Pro Xaa Leu Xaa Trp Xaa
1               5
```

```
<210> SEQ ID NO 32
<211> LENGTH: 12
<212> TYPE: PRT
<213> ORGANISM: Human immunodeficiency virus type 1
<220> FEATURE:
<221> NAME/KEY: MISC_FEATURE
<222> LOCATION: (4)..(4)
<223> OTHER INFORMATION: Xaa can be Arg, Lys, Ser or Asn
<220> FEATURE:
<221> NAME/KEY: MISC_FEATURE
<222> LOCATION: (6)..(6)
<223> OTHER INFORMATION: Xaa can be Glu or Asp
<220> FEATURE:
<221> NAME/KEY: MISC_FEATURE
<222> LOCATION: (8)..(8)
<223> OTHER INFORMATION: Xaa can be Lys or Asn

<400> SEQUENCE: 32

Val Asp Pro Xaa Leu Xaa Trp Xaa His Pro Gly Ser
 1               5                  10

<210> SEQ ID NO 33
<211> LENGTH: 7
<212> TYPE: PRT
<213> ORGANISM: Human immunodeficiency virus type 1

<400> SEQUENCE: 33

Val Asp Pro Arg Leu Glu Pro
 1               5

<210> SEQ ID NO 34
<211> LENGTH: 7
<212> TYPE: PRT
<213> ORGANISM: Human immunodeficiency virus type 1

<400> SEQUENCE: 34

Val Asp Pro Lys Leu Glu Pro
 1               5

<210> SEQ ID NO 35
<211> LENGTH: 7
<212> TYPE: PRT
<213> ORGANISM: Human immunodeficiency virus type 1

<400> SEQUENCE: 35

Val Asp Pro Ser Leu Glu Pro
 1               5

<210> SEQ ID NO 36
<211> LENGTH: 7
<212> TYPE: PRT
<213> ORGANISM: Human immunodeficiency virus type 1

<400> SEQUENCE: 36

Val Asp Pro Asn Leu Glu Pro
 1               5

<210> SEQ ID NO 37
<211> LENGTH: 7
<212> TYPE: PRT
<213> ORGANISM: Human immunodeficiency virus type 1

<400> SEQUENCE: 37

Val Asp Pro Arg Leu Asp Pro
 1               5
```

```
<210> SEQ ID NO 38
<211> LENGTH: 7
<212> TYPE: PRT
<213> ORGANISM: Human immunodeficiency virus type 1

<400> SEQUENCE: 38

Val Asp Pro Lys Leu Asp Pro
1               5

<210> SEQ ID NO 39
<211> LENGTH: 7
<212> TYPE: PRT
<213> ORGANISM: Human immunodeficiency virus type 1

<400> SEQUENCE: 39

Val Asp Pro Ser Leu Asp Pro
1               5

<210> SEQ ID NO 40
<211> LENGTH: 7
<212> TYPE: PRT
<213> ORGANISM: Human immunodeficiency virus type 1

<400> SEQUENCE: 40

Val Asp Pro Asn Leu Asp Pro
1               5

<210> SEQ ID NO 41
<211> LENGTH: 14
<212> TYPE: PRT
<213> ORGANISM: Human immunodeficiency virus type 1

<400> SEQUENCE: 41

Phe Ser Asp Tyr Tyr Met Ser Trp Ile Arg Gln Ala Pro Gly
1               5                   10
```